US009901256B2

(12) United States Patent
Seibel et al.

(10) Patent No.: US 9,901,256 B2
(45) Date of Patent: Feb. 27, 2018

(54) DENTAL DEMINERALIZATION DETECTION, METHODS AND SYSTEMS

(71) Applicant: University of Washington through its Center for Commercialization, Seattle, WA (US)

(72) Inventors: Eric J. Seibel, Seattle, WA (US); Liang Zhang, Seattle, WA (US); Richard S. Johnston, Sammamish, WA (US); Charles D. Melville, Camano Island, WA (US); Leonard Nelson, Seattle, WA (US); Cameron M. Lee, Seattle, WA (US); Joel Berg, Bellevue, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 303 days.

(21) Appl. No.: 14/372,388

(22) PCT Filed: Jan. 18, 2013

(86) PCT No.: PCT/US2013/022286
§ 371 (c)(1),
(2) Date: Jul. 15, 2014

(87) PCT Pub. No.: WO2013/109978
PCT Pub. Date: Jul. 25, 2013

(65) Prior Publication Data
US 2015/0010878 A1   Jan. 8, 2015

Related U.S. Application Data

(60) Provisional application No. 61/588,809, filed on Jan. 20, 2012.

(51) Int. Cl.
*A61B 5/00* (2006.01)
*G01J 3/10* (2006.01)
(Continued)

(52) U.S. Cl.
CPC ........ *A61B 5/0088* (2013.01); *A61B 1/00009* (2013.01); *A61B 1/00096* (2013.01);
(Continued)

(58) Field of Classification Search
CPC ........... A61C 19/04; A61B 5/0534; G01J 3/40
(Continued)

(56) References Cited

U.S. PATENT DOCUMENTS 4,479,449 A   10/1984   Alfano
RE31,815 E *   1/1985   Alfano ................. A61B 5/0088
356/237.1
(Continued)

FOREIGN PATENT DOCUMENTS

WO   WO 98/52460 A1   11/1998

OTHER PUBLICATIONS

Hibst, et al. Detection of occlusal caries by laser fluorescence: basic and clinical investigations. Medical Laser Application. 2001; 16(3):205-213.
(Continued)

*Primary Examiner* — Nicholas Lucchesi
(74) *Attorney, Agent, or Firm* — Christensen O'Connor Johnson Kindness PLLC

(57) ABSTRACT

Methods and systems for detecting early stage dental caries and decays are provided. In particular, in an embodiment, laser-induced autofluorescence (AF) from multiple excitation wavelengths is obtained and analyzed. Endogenous fluorophores residing in the enamel naturally fluoresce when illuminated by wavelengths ranging from ultraviolet into the visible spectrum. The relative intensities of the AF emission
(Continued)

changes between different excitation wavelengths when the enamel changes from healthy to demineralized. By taking a ratio of AF emission spectra integrals between different excitation wavelengths, a standard is created wherein changes in AF ratios within a tooth are quantified and serve as indicators of early stage enamel demineralization. The techniques described herein may be used in conjunction with a scanning fiber endoscope (SFE) to provide a reliable, safe and low-cost means for identifying dental caries or decays.

20 Claims, 18 Drawing Sheets

(51) Int. Cl.
| | |
|---|---|
| G01N 21/64 | (2006.01) |
| G01J 3/02 | (2006.01) |
| G01J 3/06 | (2006.01) |
| G01J 3/44 | (2006.01) |
| A61B 1/00 | (2006.01) |
| A61B 1/015 | (2006.01) |
| A61B 1/07 | (2006.01) |
| A61B 1/247 | (2006.01) |
| A61C 19/04 | (2006.01) |

(52) U.S. Cl.
CPC .......... *A61B 1/00142* (2013.01); *A61B 1/015* (2013.01); *A61B 1/07* (2013.01); *A61B 1/247* (2013.01); *A61B 5/0071* (2013.01); *A61B 5/0075* (2013.01); *A61B 5/0084* (2013.01); *A61B 5/4547* (2013.01); *A61C 19/04* (2013.01); *G01J 3/0205* (2013.01); *G01J 3/0218* (2013.01); *G01J 3/06* (2013.01); *G01J 3/10* (2013.01); *G01J 3/4406* (2013.01); *G01N 21/645* (2013.01); *G01N 21/6486* (2013.01); *G01N 2021/6421* (2013.01); *G01N 2021/6484* (2013.01); *G01N 2021/6493* (2013.01)

(58) Field of Classification Search
USPC .................................................... 433/29, 215
See application file for complete search history.

(56) References Cited

U.S. PATENT DOCUMENTS

| | | | |
|---|---|---|---|
| 4,515,476 A | 5/1985 | Ingmar | |
| 5,345,941 A | 9/1994 | Rava et al. | |
| 5,382,163 A * | 1/1995 | Putnam .................. | A61C 19/04 433/215 |
| 5,413,108 A | 5/1995 | Alfano | |
| 5,450,293 A | 9/1995 | Hoffman | |
| 5,483,951 A | 1/1996 | Frassica et al. | |
| 5,816,676 A | 10/1998 | Koenen Meyers et al. | |
| 6,024,562 A * | 2/2000 | Hibst .................... | A61B 5/0088 433/29 |
| 6,186,780 B1 * | 2/2001 | Hibst .................... | A61B 5/0088 433/215 |
| 6,231,338 B1 | 5/2001 | de Josselin de Jong et al. | |
| 6,294,775 B1 | 9/2001 | Seibel et al. | |
| 6,563,105 B2 | 5/2003 | Seibel et al. | |
| 6,571,118 B1 | 5/2003 | Utzinger et al. | |
| 6,584,341 B1 * | 6/2003 | Mandelis ............. | A61B 5/0088 433/29 |
| 6,615,068 B1 * | 9/2003 | Alfano ................. | A61B 5/0059 250/459.1 |
| 6,821,116 B2 | 11/2004 | Severance | |
| 6,975,898 B2 | 12/2005 | Seibel | |
| 7,475,821 B2 | 1/2009 | Barkan et al. | |
| 7,942,814 B2 | 5/2011 | Remijan et al. | |
| 7,955,076 B2 * | 6/2011 | Yamagishi ........... | A61B 5/0088 433/29 |
| 8,027,709 B2 * | 9/2011 | Arnone ................ | A61B 5/0088 433/29 |
| 8,182,479 B2 | 5/2012 | Schneider | |
| 8,184,147 B2 | 5/2012 | Crucs et al. | |
| 8,224,045 B2 | 7/2012 | Burns et al. | |
| 8,285,039 B2 | 10/2012 | Komiya | |
| 8,371,848 B2 * | 2/2013 | Okawa .................... | A61B 1/24 433/29 |
| 8,556,625 B2 * | 10/2013 | Lovely ................. | A61B 5/0088 382/128 |
| 8,992,216 B2 * | 3/2015 | Karazivan ............ | A61B 5/0088 356/243.8 |
| 9,060,690 B2 * | 6/2015 | Liang ................... | A61B 1/0638 |
| 2004/0220498 A1 | 11/2004 | Li et al. | |
| 2004/0240716 A1 | 12/2004 | de Josselin de Jong et al. | |
| 2005/0202363 A1 | 9/2005 | Osterwalder | |
| 2005/0283058 A1 | 12/2005 | Choo-Smith et al. | |
| 2007/0134615 A1 | 6/2007 | Lovely | |
| 2008/0248447 A1 | 10/2008 | Karazivan | |
| 2009/0048648 A1 | 2/2009 | Dacey, Jr. et al. | |
| 2009/0055024 A1 | 2/2009 | Kay | |
| 2011/0090513 A1 | 4/2011 | Seidl et al. | |
| 2011/0117025 A1 | 5/2011 | Dacosta et al. | |
| 2013/0323674 A1 | 12/2013 | Hakomori et al. | |
| 2015/0005596 A1 | 1/2015 | Wilzbach | |
| 2015/0010878 A1 | 1/2015 | Seibel et al. | |
| 2015/0216398 A1 | 8/2015 | Yang et al. | |

OTHER PUBLICATIONS

International preliminary report on patentability dated Jul. 22, 2014 for PCT/US2013/022286.
International search report and written opinion dated Apr. 10, 2013 for PCT/US2013/022286.
Schoenly, et al. Near-UV laser treatment of extrinsic dental enamel stains. Lasers in Surgery and Medicine. 2012; 44:339-345.
Shakibaie, et al. Applications of laser induced fluorescence in dentistry. International Journal of Dental Clinics. 2011; 3(3):38-44.
Thomas. Spectroscopic investigation of tooth caries and demineralization. Dated May 20, 2009. http://dyuthi.cusat.ac.in/xmlui/bitstream/handle/purl/1980/Dyuthi-T0456.pdf?sequence=22.
Walsh, et al. Ultraviolet-induced fluorescence: shedding new light on dental biofilms and dental caries. Australasian Dental Practice Magazine. Nov./Dec. 2007.
Zhang, et al. Red-shifted fluorescence of sound dental hard tissue. Journal of Biomedical Optics. 2011; 16(7):071411.
Zhang, et al. Spectrally enhanced imaging of occlusal surfaces and artificial shallow enamel erosions with a scanning fiber endoscope. Journal of Biomedical Optics. 2012; 17(7):076019.
Zuluaga, et al. Fluorescence excitation emission matrices of human tissue: a system for in vivo measurement and method of data analysis. Applied Spectroscopy. 1999; 53(3):302-311.
D. Spitzer et al., "The Absorption and Scattering of Light in Bovine and Human Dental Enamel," Calcified Tissue Research, 17(2):129-137 (1975).
JBD Featherstone et al., "A Mechanism for Dental Caries Based on Chemical Processes and Diffusion Phenomena During In-Vitro Caries Simulation on Human Tooth Enamel," Archives of Oral Biology, 24(2):101-112 (1979).
SA Prahl et al., "A Monte Carlo Model of Light Propagation in Tissue," SPIE Proceedings of Dosimetry of Laser Radiation in Medicine and Biology, IS 5:102-111 (1989).
L. Giniunas et al., "Endoscope With Optical Sectioning Capability," Applied Optics, 32(16):2888-2890 (1993).
D. Fried et al., "Nature of Light Scattering in Dental Enamel and Dentin at Visible and Near-Infrared Wavelengths," Applied Optics, 34(7):1278-1285 (1995).
LH Wang et al., "MCML—Monte Carlo Modeling of Photon Transport in Multi-Layered Tissues," Computer Methods and Programs in Biomedicine, 47(2):131-146 (1995).
JR Zijp et al., "HeNe-Laser Light Scattering by Human Dental Enamel," Journal of Dental Research, 74(12):1891-1898 (1995).
OM Winn et al., "Coronal and Root Caries in the Dentition of Adults in the United States, 1988-1991," Journal of Dental Research, 75:642-651 (1996).

(56) References Cited

OTHER PUBLICATIONS

KJ Anusavice., "Management of Dental Caries as a Chronic Infectious Disease," Journal of Dental Education, 62(10):791-802 (1998).
BW Colston Jr et al., "Dental OCT," Optics Express, 3(6):230-238 (1998).
BW Colston Jr et al., "Imaging of Hard- and Soft-Tissue Structure in the Oral Cavity by Optical Coherence Tomography," Applied Optics, 37(16):3582-3585 (1998).
KR Ekstrand et al., "Detection, Diagnosing, Monitoring and Logical Treatment of Occlusal Caries in Relation to Lesion Activity and Severity. An In Vivo Examination With Histological Validation," Caries Research, 32(4):247-254 (1998).
F. Feldchtein et al., "In Vivo OCT Imaging of Hard and Soft Tissue of the Oral Cavity," Optics Express, 3(6):239-250 (1998).
Ferreira Zandona et al., "Laser Fluorescence Detection of Demineralization in Artificial Occlusal Fissures," Caries Research, 32(1):31-40 (1998).
AG Almeida et al., "Future Caries Susceptibility in Children With Early Childhood Caries Following Treatment Under General Anesthesia," Pediatric Dentistry, 22(4):302-306 (2000).
FLL Otis et al., "Optical Coherence Tomography: A New Imaging Technology for Dentistry," Journal of the American Dental Association, 131(4):511-514 (2000).
C. Robinson et al., "The Chemistry of Enamel Caries," Critical Reviews in Oral Biology and Medicine, 11(4):481-495 (2000).
J. Bush et al., "All-Fiber Optic Coherence Domain Interferometric Techniques," Fiber Optic Sensor Technology II, 4204:71-80 (2001).
J. Knittel et al., "Endoscope-Compatible Confocal Microscope Using a Gradient Index-Lens System,'" Optics Communications, 188(5-6):267-273 (2001).
P. Niederer et al., "Image Quality of Endoscopes," Biomonitoring and Endoscopy Technologies, Proceedings of SPIE, 4158:1-10 (2001).
EJ Seibel et al., "'Single Fiber Flexible Endoscope: General Design for Small Size, High Resolution, and Wide Field of View," Biomonitoring and Endoscopy Technologies, Proceedings of SPIE, 4158:29-39 (2001).
QYJ Smithwick et al., "Control Aspects of the Single Fiber Scanning Endoscope,'" Optical Fibers and Sensors for Medical Applications, Proceedings of SPIE, 4253:176-188 (2001).
ME Fauver et al., "Microfabrication of Fiber Optic Scanners," Optical Scanning 2002, Proceedings of SPIE, 4773:102-110 (2002).
D Fried et al., "Imaging Caries Lesions and Lesion Progression With Polarization Sensitive Optical Coherence Tomography," Journal of Biomedical Optics, 7(4):618-627 (2002).
D. Fried et al., "Imaging Caries Lesions and Lesion Progression With Polarization-Sensitive Optical Coherence Tomography," Lasers in Dentistry VIII, 4610:113-124 (2002).
RS Jones et al., "Attenuation of 1310- and 1550-nm Laser Light Through Sound Dental Enamel," Lasers in Dentistry VIII, 4610:187-190 (2002).
EJ Seibel et al., "Prototype Scanning Fiber Endoscope," Optical Fibers and Sensors for Medical Applications II, Proceedings of the SPIE, 4616:173-179 (2002).
EJ Seibel et al., "Unique Features of Optical Scanning, Single Fiber Endoscopy," Lasers in Surgery and Medicine, 30(3):177-183 (2002).
QYJ Smithwick et al., "Depth Enhancement Using a Scanning Fiber Optical Endoscope," Optical Biopsy IV, Proceedings of SPIE, 4613:222-233 (2002).
N Tinanoff et al., "Clinical Decision Making for Caries Management in Children," Pediatric Dentistry, 24(5):386-392 (2002).
AI Ismail, "Determinants of Health in Children and the Problem of Early Childhood Caries," Pediatric Dentistry, 25(4):328-333 (2003).
RS Jones et al., "Near-Infrared Transillumination at 1310-nm for the Imaging of Early Dental Decay," Optics Express, 11(18):2259-2265 (2003).
RO Rocha et al., "In Vivo Effectiveness of Laser Fluorescence Compared to Visual Inspection and Radiography for the Detection of Occlusal Caries in Primary Teeth," Caries Research, 37(6):437-441 (2003).
JD Bader et al., "A Systematic Review of the Performance of a Laser Fluorescence Device for Detecting Caries," Journal of the American Dental Association, 135(10):1413-1426 (2004).
K Carter et al., "Automated Quantification of Dental Plaque Accumulation Using Digital Imaging," Journal of Dentistry, 32(8):623-628 (2004).
PR Gomes et al., "Dental Caries in Paulinia, Sao Paulo State, Brazil, and WHO Goals for 2000 and 2010," Cad Saude Publica, 20(3):866-870 (2004).
GC Jones et al., "Transillumination of Interproximal Caries Lesions with 830-nm Light," Lasers in Dentistry X, 5313:17-22 (2004).
RS Jones et al., "Imaging Artificial Caries Under Composite Sealants and Restorations," Journal of Biomedical Optics, 9(6):1297-1304 (2004).
CM Bühler et al., "Imaging of Occlusal Dental Caries (Decay) with Near-IR Light at 1310-nm," Optics Express, 13(2):573-582 (2005).
D Fried et al., "Early Caries Imaging and Monitoring With Near-Infrared Light," Dental Clinics of North America, 49(4):771-793 (2005).
JC Hamilton "Should a Dental Explorer Be Used to Probe Suspected Lesions?" Journal of the American Dental Association, 136(11):1526-1532 (2005).
RS Jones et al., "The Effect of High-Index Liquids on PS-OCT Imaging of Dental Caries," Lasers in Dentistry XI, 5687:34-41 (2005).
P Ngaotheppitak et al., "Measurement of the Severity of Natural Smooth Surface (Interproximal) Caries Lesions with Polarization Sensitive Optical Coherence Tomography," Lasers in Surgery and Medicine, 37(1):78-88 (2005).
CM Brown et al., "Optomechanical Design and Analysis for a Scanning Fiber Endoscope," Proceedings of the 2001 ASME International Mechanical Engineering Congress and Exposition, 51:165-166 (2006).
CL Darling et al., "Light Scattering Properties of Natural and Artificially Demineralized Dental Enamel at 1310 nm," Journal of Biomedical Optics, 11(3):034023 (2006).
EK Delgado-Angulo et al., "Influence of Host Related Indicators on Dental Caries in the Permanent Dentition," Acta Odontal Latinoam, 19(2):85-92 (2006).
RS Jones et al., "Remineralization of Enamel Caries Can Decrease Optical Reflectivity," Journal of Dental Research, 85(9):804-808 (2006).
RS Jones et al., "Imaging Artificial Caries on the Occlusal Surfaces With Polarization-Sensitive Optical Coherence Tomography," Caries Research, 40(2):81-89 (2006).
RS Jones et al., "Remineralization of In Vitro Dental Caries Assessed With Polarization-Sensitive Optical Coherence Tomography," Journal of Biomedical Optics, 11(1):014016-1-9 (2006).
P Ngaotheppitak et al., "PS-OCT of Occlusal and Interproximal Caries Lesions Viewed From Occlusal Surfaces," Lasers in Dentistry X, 6137:61370L-1-8 (2006).
T Al et al., "Risk Indicators for Childhood Caries in Taiwan," Community Dentistry and Oral Epidemiology, 34(6):437-445 (2006).
AF Zandona et al., "Diagnostic Tools for Early Caries Detection," Journal of the American Dental Association, 137(12):1675-1684 (2006).
SL Chong et al., "Nondestructive Measurement of the Inhibition of Demineralization on Smooth Surfaces Using Polarization-Sensitive Optical Coherence Tomography," Lasers in Surgery and Medicine, 39(5):422-427 (2007).
M Du et al., "Caries in Preschool Children and Its Risk Factor in 2 Provinces in China," Quintessence International, 38(2):143-151 (2007).
D Fried et al.,"Polarization Sensitive Optical Coherence Tomography for Quantifying the Severity of Natural Caries Lesions on Occlusal Surfaces," Lasers in Dentistry XIII, 6425:64250U-1-8 (2007).

(56) References Cited

OTHER PUBLICATIONS

JS Greenspan et al., "A Global Theme—Poverty and Human Development," Journal of Dental Research, 86(10):917-918 (2007).
S Naidoo et al., "Nutrition, Oral Health and the Young Child," Maternal and Child Nutrition, 3(4):312-321 (2007).
HD Sgan-Cohen et al., "Health, Oral Health and Poverty," Journal of the American Dental Association, 138(11):1437-1442 (2007).
E Barberia et al., "A Clinical Study of Caries Diagnosis With a Laser Fluorescence System," Journal of the American Dental Association, 139(5):572-579 (2008).
K Hirasuna et al., "Near-Infrared Imaging of Developmental Defects in Dental Enamel," Journal of Biomedical Optics, 13(4):044011-1-7 (2008).
JA Rodrigues et al., "The Influence of Zero-Value Subtraction on the Performance of Two Laser Fluorescence Devices for Detecting Occlusal Caries in Vivo," Journal of the American Dental Association, 139(8):1105-1112 (2008).
B Valera et al., "Comparison of Visual Inspection, Radiographic Examination, Laser Fluorescence and Their Combinations on Treatment Decisions for Occlusal Surfaces," American Journal of Dentistry, 21(1):25-29 (2008).
L Coulthwaite et al., "Evaluation of in Vivo Denture Plaque Assessment Methods," British Dental Journal, 207(6):E12, 6 pages (2009).
L Coulthwaite et al., "QLF is Not Readily Suitable for in Vivo Denture Plaque Assessment," Journal of Dentistry, 37(11):898-901 (2009).
JD Featherstone., "Remineralization, the Natural Caries Repair Process—the Need for New Approaches," Advances in Dental Research, 21(1):4-7 (2009).
LE Kagihara et al., "Assessment, Management, and Prevention of Early Childhood Caries," Journal of the American Academy of Nurse Practitioners, 21(1):1-10 (2009).
C Lee et al., "Non-Destructive Measurement of Demineralization and Remineralization in the Occlusal Pits and Fissures of Extracted 3rd Molars with PS-OCT," Lasers in Dentistry XV, 7162:71620V-1-6 (2009).
C Lee et al., "Polarization-Sensitive Optical Coherence Tomographic Imaging of Artificial Demineralization on Exposed Surfaces of Tooth Roots," Dental Materials, 25(6):721-728 (2009).
D Lee et al., "Near-IR Multi-Modal Imaging of Natural Occlusal Lesions," Lasers in Dentistry XV, 7162:71620X-1-7 (2009).
CH Silva-Lovato et al., "Evaluation of a Computerized Method for Denture Biofilm Quantification: Inter-Examiner Reproducibility," Journal of Prosthodontics, 18(4):332-336 (2009).
SK Manesh et al., "Nondestructive Assessment of Dentin Demineralization Using Polarization-Sensitive Optical Coherence Tomography After Exposure to Fluoride and Laser Irradiation," Journal of Biomedical Materials Research B: Applied Biomaterials, 90(2):802-812 (2009).
SK Manesh et al., "Polarization-Sensitive Optical Coherence Tomography for the Nondestructive Assessment of the Remineralization of Dentin," Journal of Biomedical Optics, 14(4):044002-1-6 (2009).
SM Douglas et al., "Imaging Natural Occlusal Caries Lesions With Optical Coherence Tomography," Lasers in Dentistry XVI, 7549:75490N-1-7 (2010).
D Fried., "Lasers and Optics Measuring Tooth Decay," Optics & Photonics News, pp. 15-19 (2010).
C Lee et al., "In Vitro Near-Infrared Imaging of Occlusal Dental Caries Using a Germanium-Enhanced CMOS Camera," Lasers in Dentistry XVI, 7549:75490K-1-7 (2010).
C Lee et al., "Nondestructive Assessment of the Severity of Occlusal Caries Lesions With Near-Infrared Imaging at 1310 NM," Journal of Biomedical Optics, 15(4):047011-1-7 (2010).
CM Lee et al., "Scanning Fiber Endoscopy With Highly Flexible, 1 MM Catheterscopes for Wide-Field, Full-Color Imaging," Journal of Biophotonics. 3(5-6):385-407 (2010).
CM Lee et al., "Wide Field Fluorescence Imaging in Narrow Passageways Using Scanning Fiber Endoscope Technology," Endoscopic Microscopy V, Proceedings of SPIE, 7558:755806-1-10 (2010).
T Louie et al., "Clinical Assessment of Early Tooth Demineralization Using Polarization Sensitive Optical Coherence Tomography," Lasers in Surgery and Medicine, 42(10):738-745 (2010).
M Staninec et al., "In Vivo Near-IR Imaging of Approximal Dental Decay at 1,310 NM," Lasers in Surgery and Medicine, 42(4):292-298 (2010).
MAB Blank et al., "Laser Scanning Dental Probe for Endodontic Root Canal Treatment," Lasers in Dentistry XVII, Proceedings of SPIE 2011, 7884:788403-1-7 (2011).
CK Hope et al., "Photobleaching of Red Fluorescence in Oral Biofilms," Journal of Periodontal Research, 46(2):228-234 (2011).
National Institute of Dental and Craniofacial Research., "Dental Caries (Tooth Decay) in Children (Age 2 to 11)," NIDCRF (2011).
EJ Seibel et al., "Multimodal Flexible Cystoscopy for Creating Co-Registered Panoramas of the Bladder Urothelium," Photonic Therapeutics and Diagnostics VIII, Proceedings of SPIE, 8207:82071A-1-7 (2012).
FTD Soper et al., "Surface Mosaics of the Bladder Reconstructed From Endoscopic Video for Automated Surveillance," IEEE Transactions on Biomedical Engineering, 59(6):1670-1680 (2012).
L Zhang et al., "Spectrally Enhanced Image Resolution of Tooth Enamel Surfaces," Lasers in Dentistry XVIII, Proceedings of SPIE, 8208:82080E-1-15 (2012).
L Zhang et al., "Optical Measure of Enamel Health," 2012 IEEE Global Humanitarian Technology Conference, pp. 345-349 (2012).
C Yang et al., "Mitigating Fluorescence Spectral Overlap in Wide-Field Endoscopic Imaging," Journal of Biomedical Optics, 18(8):086012-1-13 (2013).
C Yang et al., "Color-Matched and Fluorescence-Labeled Esophagus Phantom and Its Applications," Journal of Biomedical Optics, 18(2):026020-1-11 (2013).
L Zhang et al., "Tri-Modal Detection of Early Childhood Caries Using Laser Light Scanning and Fluorescence Spectroscopy—Clinical Prototype," Journal of Biomedical Optics, 18(11):111412-1-8 (2013).
C Yang et al., "Target-To-Background Enhancement in Multispectral Endoscopy with Background Autofluorescence Mitigation for Quantitative Molecular Imaging," Journal of Biomedical Optics, 19(7):076014-1-16 (2014).
Wikipedia., "Methylene blue," available online at: http://en.wikipedia.org/wiki/Methylene_blue (2016).
CM Brown et al., "Mechanical Design and Analysis for a Scanning Fiber Endoscope," Proceedings of the 2001 ASME International Mechanical Engineering Congress and Exposition, 51:165-166 (2001).

* cited by examiner

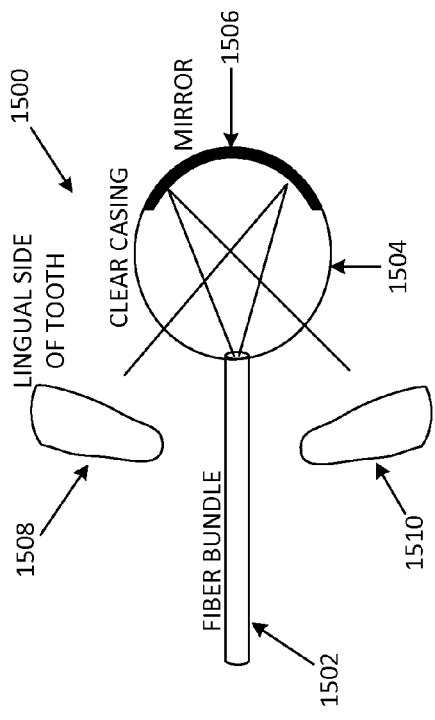
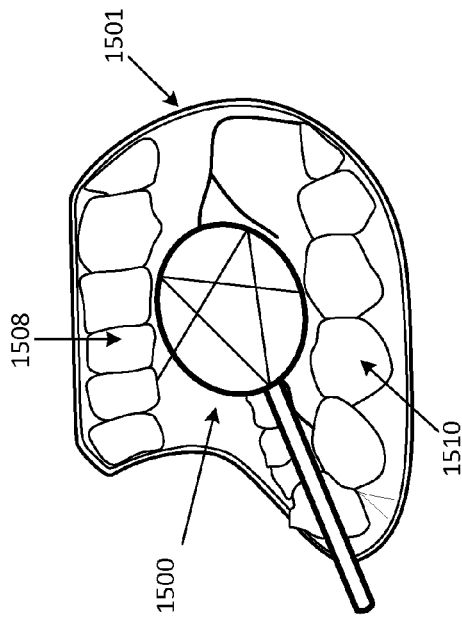
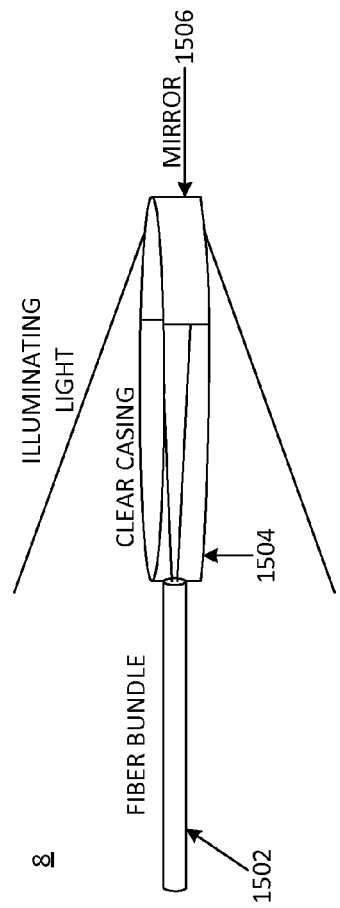
FIG. 15b
FIG. 15c
FIG. 15a

DENTAL DEMINERALIZATION DETECTION, METHODS AND SYSTEMS

CROSS-REFERENCE

This application is a U.S. National Phase Application under 35 U.S.C. § 371 of International Application No. PCT/US2013/022286, filed Jan. 18, 2013, which claims the benefit of U.S. Provisional Application No. 61/588,809 filed Jan. 20, 2012, which application is incorporated herein by reference.

STATEMENT AS TO FEDERALLY SPONSORED RESEARCH

This invention was made with government support under 1 R21 CA094303-01A1 awarded by the National Institutes of Health. The government has certain rights in the invention.

BACKGROUND OF THE INVENTION

Tooth decay is initiated by bacterial acids that destroy a region of the outer enamel layer of a tooth. This results in demineralization of the enamel sub-surface and surface leading to cavitation once the outer enamel layer is no longer structurally viable. At this point the tooth will require a filling. If this acid etching process reaches the underlying and more porous dentin, a more serious destruction occurs that could require extraction of the tooth and at best the tooth will require a more invasive filling. Typically at this point the cavity can be seen on X-ray and often by eye or by tactile probing with a dental explorer. However, if this demineralization process can be detected and monitored by optical imaging, then tooth decay may be managed, for example, by improving dental hygiene or pharmaceutically induced remineralization therapy.

X-ray and visual inspection often lacks the sensitivity to detect lesions at an early enough stage where remineralization is possible. In addition, repetitive monitoring of suspected demineralization by X-ray imaging may be not safe to use for children. Other detection means such as using ultrasound technologies may lack sufficient sensitivity and specificity, be bulky and expensive. Therefore, a need exists for a reliable, non-invasive and cost-effective means for identifying dental caries.

SUMMARY OF THE INVENTION

Methods and structures for detecting early stage dental decay or demineralization are provided. A method includes directing excitation light at two or more wavelengths to a dental area, obtaining autofluorescence (AF) emission spectral information such as spectral integrals respectively associated with the two or more wavelengths, obtaining a value such as a ratio indicating a relationship between the emission spectral information respectively associated with the two or more wavelengths, and determining the dental health associated with the dental area based at least in part on the value. The method may be used in conjunction with other imaging means to enhance reliability.

In an embodiment, the detected dental condition as well as other indications may be displayed directly onto a tooth to aid visual inspection of the tooth.

In an embodiment, a method for reducing specular reflection in imaging may be provided. The method may include detecting reflectance or fluorescence with one or more sets of photodetectors and analyzing one or more sets of data associated with the one or more sets of detectors. If any set of data includes saturated data (potentially caused by specular reflection), the set of data is disregarded in the forming of the final image.

In an embodiment, a dental health screening system is provided. The system may include an illumination source configured to provide light at two or more wavelengths, a probe configured to illuminate a first dental area and a second dental area at the two or more excitation wavelengths, a spectrometer configured to provide emission spectral information respectively associated with the two or more wavelengths for the first dental area and for the second dental area, and a computer system. The computer system may be configured to obtain a first value indicating a relationship between the emission spectral information respectively associated with the two or more wavelengths for the first dental area, obtain a second value indicating a relationship between the emission spectral information respectively associated with the two or more wavelengths for the second dental area, and determine dental health associated with the second dental area based at least in part on the first value and the second value.

In an embodiment, a disposable sleeve may be provided to cover at least a portion of the probe to facilitate sterility. The sleeve may be made with a material with inherently minimal autofluorescence and may provide one or more channels for fluid, optical signals and the like.

In various embodiments, screening device specifically designed for dental screening are provided. The screening devices may take the form of toothbrush, mouthguard, lollipop or the like to facilitate the interrogation of various dental regions.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 15a-c illustrate lollipop-like screening devices, in accordance with some embodiments.

DETAILED DESCRIPTION OF THE INVENTION

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Methods and systems for detecting dental caries and decays are provided. In particular, in an embodiment, laser-induced autofluorescence (AF) from multiple excitation wavelengths is obtained and analyzed. Endogenous fluorophores residing in the enamel naturally fluoresce when illuminated by excitation wavelengths ranging from ultraviolet into the visible spectrum. The relative intensities of the AF emission changes between different excitation wavelengths when the enamel changes from healthy to demineralized. By taking a ratio of AF emission spectra integrals between different excitation wavelengths, a standard is created wherein changes in AF ratios within a tooth are quantified and serve as indicators of early stage enamel demineralization. The techniques described herein may be embodied in or used in conjunction with a scanning fiber endoscope (SFE) to provide a reliable, safe and low-cost means for identifying dental caries or decays.

Figure 1:
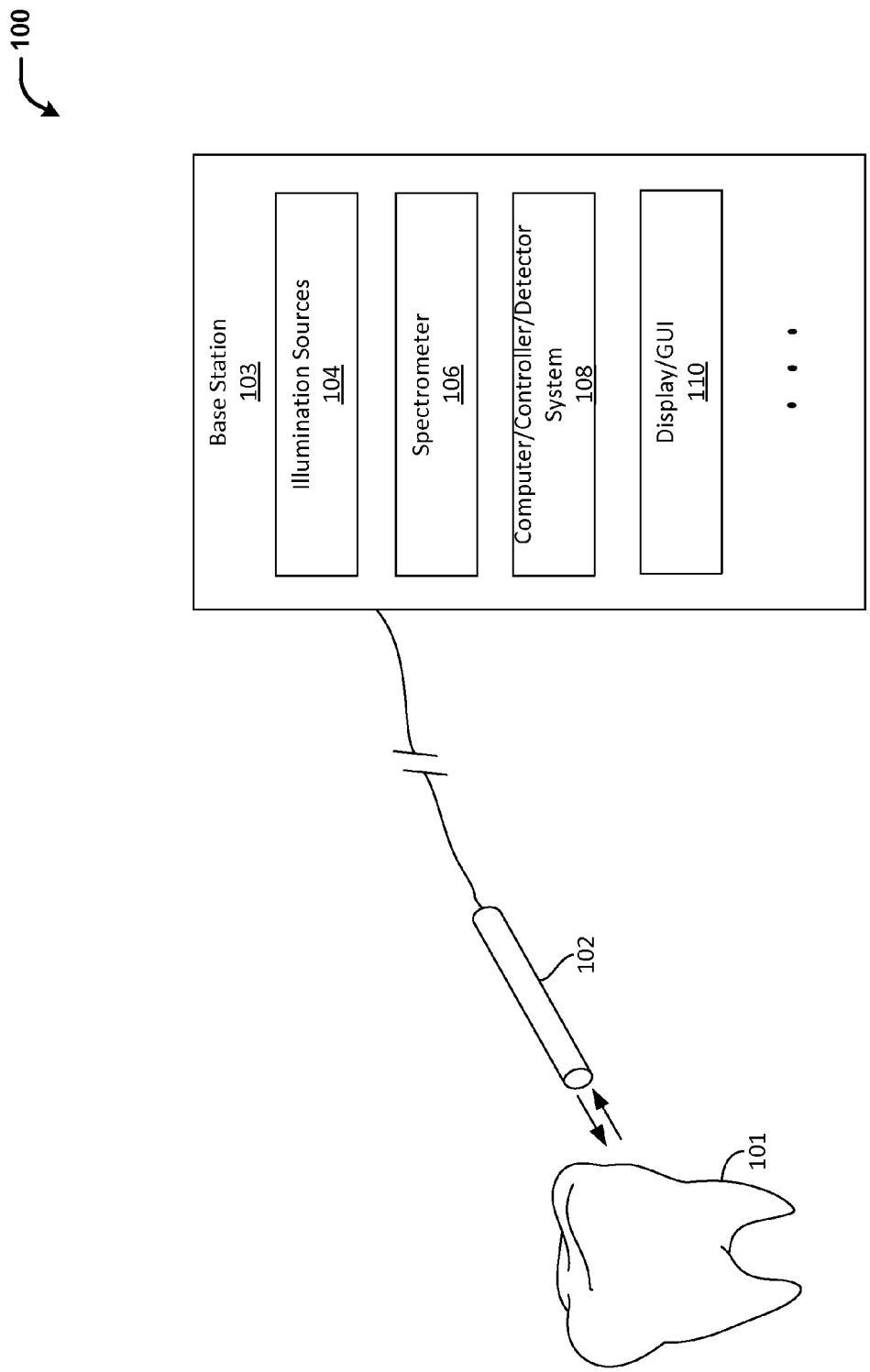
FIG. 1 illustrates components of an example dental health detection system, in accordance with an embodiment.

FIG. 1 illustrates components of an example dental health detection system 100, in accordance with an embodiment. Such a detection system may be used to by a clinician to detect the dental health related issues dental caries or decays.

Figure 2:
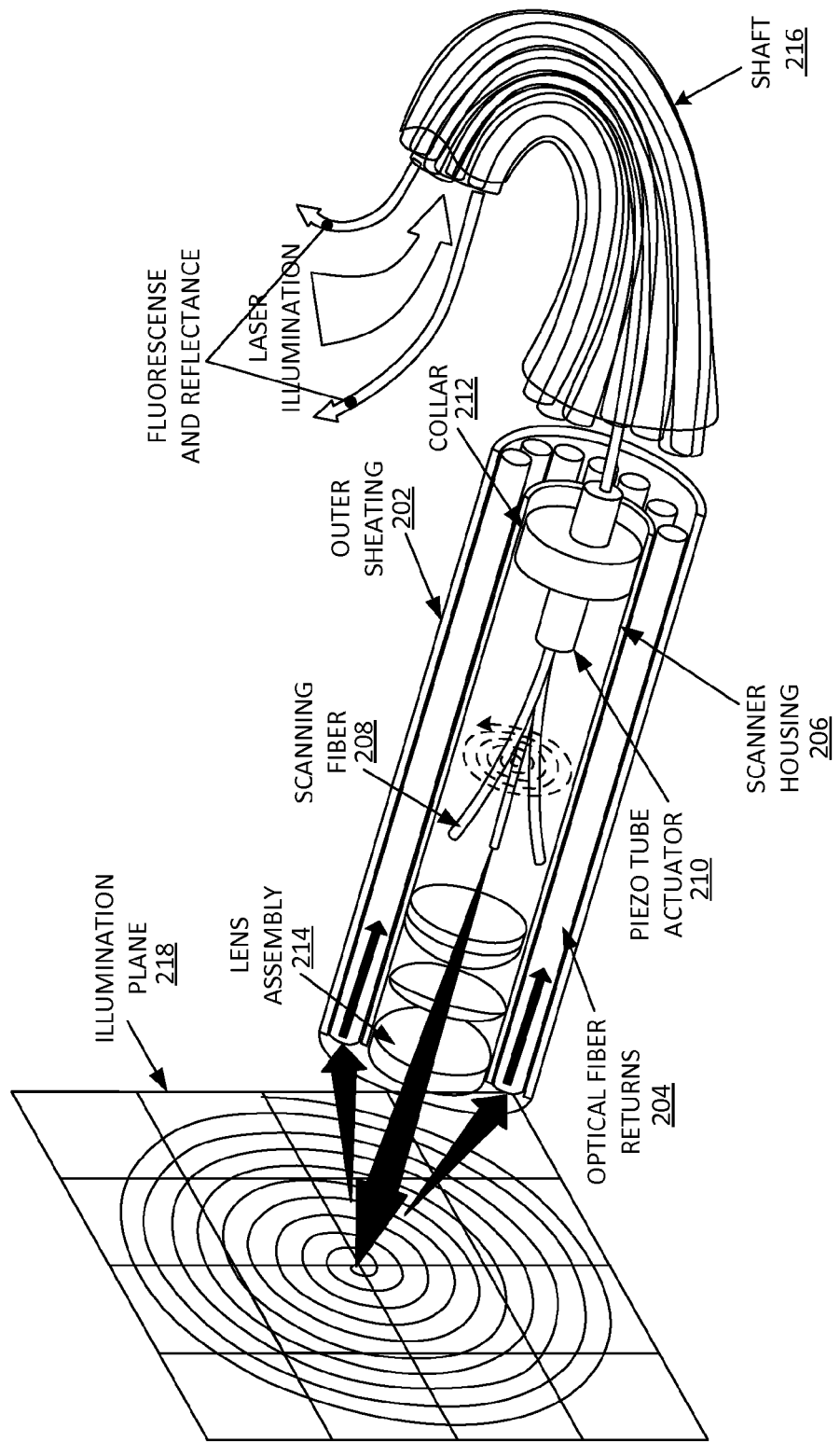
FIG. 2 illustrates example components of an Scanning Fiber Endoscope (SFE)-based embodiment of the present invention.

In an embodiment, the dental health detection system 100 includes an endoscope or a probe 102 that may be used to scan or illuminate and/or image a surface or region associated with an object 101 such a tooth. Such surface may include an occlusal (biting) surface of back teeth or the interproximal space between teeth. The probe 102 may be configured to deliver light, for example, via one or more optical fibers, toward a distal end 103 of the probe 102, for example, for illumination and/or scanning an area or region disposed proximate to the distal end of a scanning or non-scanning probe or probe 102. In addition, the probe 102 may be configured to collect, for example, via one or more collection optical fibers, reflectance and/or fluorescence light for further processing. In an embodiment, the probe 102 includes a scanning fiber endoscope (SFE) such as illustrated in FIG. 2.

In an embodiment, the probe 102 may be communicatively coupled to a base station 103 which houses one or more illumination sources 104, a spectrometer 106, a computer/controller/detector system 108 and optionally a display 110 among other components such as photodetectors (e.g., photodiodes, photomultiplier tubes (PMTs) and the like) for imaging purposes, power supplies and the like.

When in use, the illumination sources 104 may be configured to deliver light (such as laser light at various wavelengths) to a distal end of the probe 102 (e.g., via an illumination or scanning fiber). Backscattered light or fluorescence may be collected (e.g., by collection fibers included in the probe 102) and sent back (e.g., via one or more return or collection fibers) to the base station for processing and/or analysis. In an embodiment, the collected light is provided to the spectrometer 106, which may be configured to provide emission spectra information associated with various excitation wavelengths. The emission spectra information may be further analyzed by the computer/controller/detector system 108, such as to calculate the relative intensities between the two emitted AF spectra. The ratio of intensities can be used as a diagnostic standard to determine dental health. In some embodiments, the collected light may be detected by one or more photodetectors for imaging by the computer/controller/detector system 108. In various embodiments, the result of any analysis, processing, imaging, diagnosis, or treatment may be optionally displayed to a user via a display 110.

In various embodiments, an illumination source 104 may be configured to provide RGB, UV, NUV, IR, polarized, high intensity light and/or other types of light. The light may be of various wavelengths and modulated in power over time. For example, in an embodiment, the light source is configured to transmit, in time sequenced alternating fashion, laser at 405 nm and 532 nm wavelengths to the distal end of the probe (e.g., via an illumination fiber).

In various embodiments, type of the spectrometer used may depend on the requirement of the spectroscopic analysis. For example, due to the relatively broad emission spectra of the autofluorescence (AF), in some embodiments, small and low-cost microspectrometers with high dynamic range or CMOS detectors with relatively low resolution or even lower cost few wavelength spectral sensors can be used. For example, in an embodiment, a commercially available, thermoelectrically cooled CCD array based miniature fiber optic spectrometer is used. In various embodiments, the spectrometer 106 can be used to analyze and/or display fluorescence spectra in terms of fluorescence band shape, integrated area, peak amplitude and the like. In some embodiments, the spectrometer 106 may be connected to a filter to remove the excitation laser wavelengths before the collected light enters the spectrometer. In other embodiments the spectrometer can consist of Linear Variable Filter (LVF) with a linear CCD/CMOS optical detector.

In various embodiments, the computer/control system 108 may be configured to control various aspects of the dental health detection system 100 such as the frequency or pattern of a scanning fiber in the probe 102, light source selection and/or timing, input and output (I/O) of the spectrometer 106 (e.g., input and/or output thereof), the input or output (I/O) associated with the display 110 and the like. In addition, the computer/control system may be configured to perform radiometric calibration, mathematical calculations such as ratio of spectra integrals and other data processing functionalities.

In various embodiments, the computer/control system 108 comprising a memory and one or more processing units (collectively referred to as the "controller"). The memory may comprise a random access memory ("RAM"), a read only memory ("ROM"), and/or a permanent mass storage device, such as a disk drive.

The controller may be capable of executing one or more computer-executable program code stored in the memory that controls various aspects and components of the dental health detection system 100 such as described above. In some embodiments, the controller may be implemented by a simple, low-cost microprocessors or microcontroller such as Arduino. In other embodiments the controller can consist of field programmable gate arrays (FPGA) which are used to condition the fiber scanning pattern and mapping the scanned light collection into a video image files and display frames.

In various embodiments, the display 110 may optionally include one or more displays configured to provide a graphical user interface (GUI) to a user operating the dental health detection system 100. For example, the display may be configured to provide real-time images of a patient's teeth as they are being scanned, indication of dental condition of one or more tooth (e.g., whether and/or where dental caries or decays exist). For another example, the display may be used to receive and execute user commands.

In some embodiments, the computer/controller/detector system 108 may optionally include one or more data storage media for storing data received or produced by the dental health detection system 100. Such data storage media may include a floppy disc, tape drive, DVD/CD-ROM drive, memory card, USB flash drive, solid state drive (SSD) and the like.

In some embodiments, the dental health detection system 100 may include many more components than those shown in FIG. 1. However, it is not necessary that all of these generally conventional components be shown in order to disclose an illustrative embodiment.

FIG. 2 illustrates example components of an SFE-based embodiment of the present invention. The SFE illustrated may be used, in an embodiment, as part of the dental health detection system 100 discussed in connection with FIG. 1. In this embodiment, a probe or endoscope comprises an outer sheathing 202 enclosing one or more optical return fibers 204 and a scanner housing 206. The scanner housing 206 contains a portion of an illumination scanning fiber 208 coupled at a proximal end to an piezoelectric actuator 210, a collar 212 that holds the piezoelectric actually in place and a lens assembly 214 located between the distal end of the illumination scanning fiber and the distal end of the probe. The illumination scanning fiber and the collection fibers may be enclosed in a flexible shaft 216 that connects the probe to a base station (not shown).

When in use, the illumination scanning fiber may be driven by piezoelectric actuator to scan, in a predetermined pattern (e.g., spiral, zigzag), a target area on an illumination plane 218 that is proximate to the distal end of the probe. The illumination plane may be angled from the axis of the illumination and collection optical fibers by the use of a mirror or prism located distal to the illumination fiber (not shown). The scanned light may go through the lens assembly to reach the target area. Light reflected, refracted or emitted (e.g., fluorescence) may be collected by the return or collection fibers and transmitted to the base station for further analysis and processing.

In various embodiments, the SFE may be configured to provide multi-modal and multi-wavelength imaging capabilities. Such capabilities may include an intraoral color camera, high-contrast reflectance imaging of the enamel, laser-induced fluorescence (LIF) imaging of the hard dental tissue, implanted material, as well as the caries bacterial infection. Additional modalities may be provided by including near-ultra-violet (NUV) and near-infrared (NIR) laser wavelengths to achieve fluorescence lifetime imaging, photoacoustic imaging, depth resolved imaging, infrared imaging in transmission, and optical coherence tomography.

The SFE may be combined with a spectrometer to provide both imaging as well as spectroscopic capabilities. In various embodiments, the SFE may use a variety of illuminating wavelengths to perform imaging, such as near-UV wavelengths, visible, as well as near-infrared wavelengths. The imaging may be used for general surveillance and to spot regions of possible demineralization (caries or decay). Different illuminating wavelengths can be used to look for very early stage caries, later stage caries, discolorations, cracks and the like. In some embodiments, the SFE can be switched to longer wavelengths in transillumination mode so that deeper lesions and cracks can be spotted. After locating a suspicious region or during the downtime between imaging frames, point spectroscopy may be taken using multiple wavelength fluorescence. Data derived from the point spectroscopy may be used a quantitative diagnosis of dental health and structure.

In some embodiments, the probe of the SFE may be configured to be very small in size (e.g., with a rigid tip portion equivalent to a grain of rice) so that the SFE may be suitable for dental use on small children. The shaft SFE may provide long and flexible shaft that may be attached to an explorer (pick), a dental mirror or other equipment. In another case the SFE illumination and collection can be separated and embedded into the two ends of dental rope allowing transmission-mode detection of interproximal caries and decay. In some cases, the SFE may provide a non-invasive alternative to X-ray imaging and a lower-cost and less bulky alternative to camera-based and ultra-sound imaging.

Figure 3A:
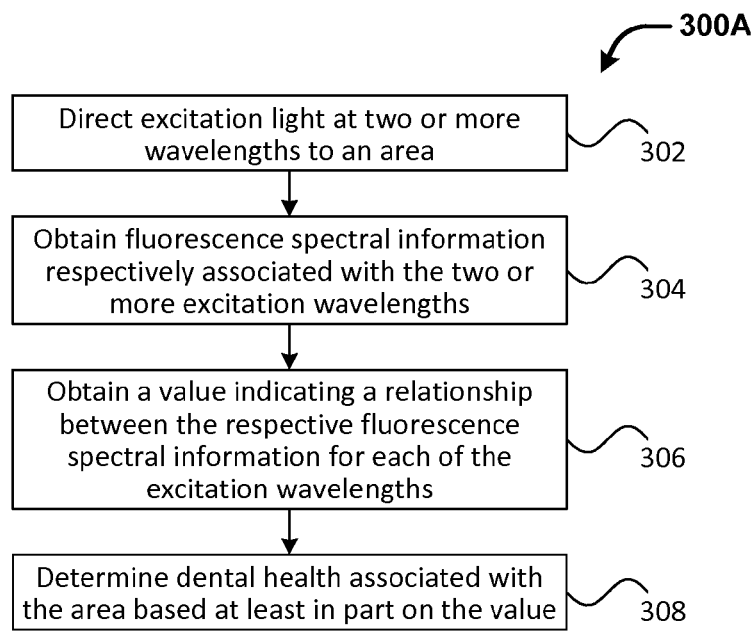
FIGS. 3a-b illustrate example processes for detecting dental caries or decays, in accordance with embodiments.
Figure 3B:
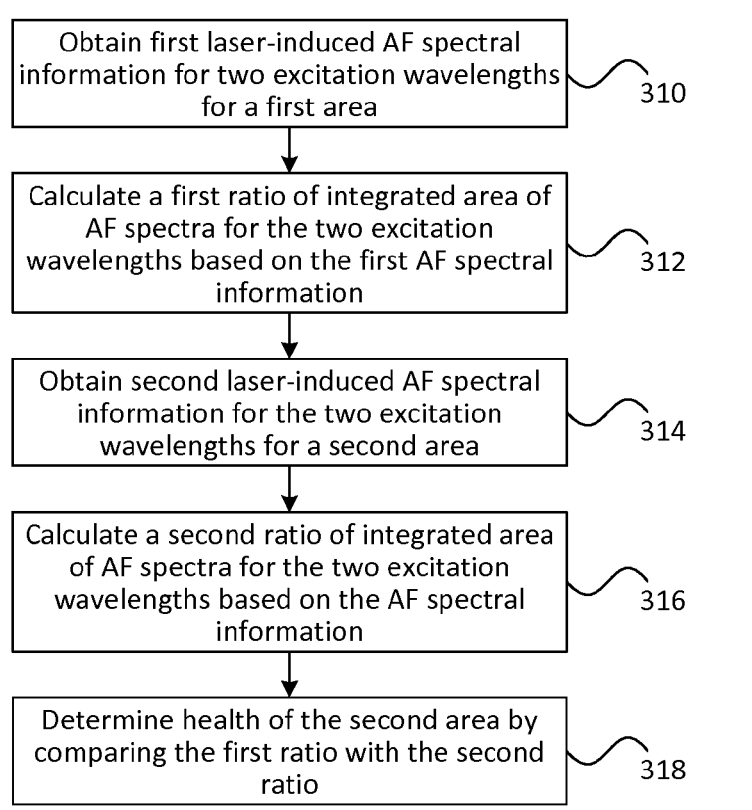

FIGS. 3a-b illustrate example processes 300a and 300b, respectively, for detecting dental caries or decays, in accordance with embodiments. Aspects of the processes 300a-b may be performed, for example, by the dental health detection system 100 discussed in connection with FIG. 1 or the SFE discussed in connection in with FIG. 2. Some or all of the processes 300a-b (or any other processes described herein, or variations and/or combinations thereof) may be performed under the control of one or more computer/control systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory. The order in which the operations are described is not intended to be construed as a limitation, and any number of the described operations can be combined in any order and/or in parallel to implement the processes.

Referring to FIG. 3a, in an embodiment, process 300A includes directing 302 excitation light (e.g., laser) at two or more distinct wavelengths to an area or region of a tooth, such as an occlusal or interproximal surface. The wavelengths may be selected based on considerations such as nature and location of dental defects, endogenous dental chromophores, exogenous dyes or particles, intensity of fluorescence, cost, and the like. For example, to detect early stage demineralization (caries), relatively short wavelength excitation lasers may be preferred because of their shallow penetration depth. In an embodiment, solid state 405 and 532 nm wavelength lasers are selected for their effective excitation of endogenous dental chromophores in addition to their low cost and convenience. Alternatively, relatively longer wavelengths (e.g. NIR) can be used for extending the penetration depth of the laser light into the dental tissues for the purpose of SFE imaging and measuring deeper regions of decay and the penetration and extent of cracks.

In an embodiment, process 300A includes obtaining reflectance measurement using scanned red (635 nm), green (532 nm), and blue (444 nm) laser light to form a visible color image of the oral cavity. The process of observing this color video image can provide the means to see discoloration of the tissues in the oral cavity, which can then direct further optical measurements. By using shorter wavelengths (e.g. NUV or 405 nm) that penetrate less deeply into the enamel, the image contrast of the laser-scanned tooth surface can be enhanced. See, for example, "Spectrally Enhanced Imaging of Occlusal Surfaces and Artificial Shallow Enamel Erosions with a Scanning Fiber Endoscope," Zhang, et al., Journal of Biomedical Optics 17(7), 076019 (July 2012), which is hereby incorporated by reference. If there are discolorations on the surface of the tooth, then higher-power UV and NUV laser illumination can be used to clear these stains by bleaching the chromaphores or destroying the absorbing species and exposing bare enamel. This therapeutic process can use either scanned or stationary beam of laser light. See, for example, "Near-UV Laser Treatment of Extrinsic Dental Enamel Stains," Schoenly, et al., Lasers in Surgery and Medicine 44:339-345 (2012).

In an embodiment, process 300A includes obtaining 304 fluorescence spectral information associated with each of the excitation wavelengths. For example, emitted fluorescence in response to each of the excitation wavelengths may be collected and transmitted (e.g., by one or more optical fibers) to a spectrometer such as the spectrometer 106 discussed in connection with FIG. 1. The spectrometer may process the received signals and provide spectral information such as an emission spectrum curve showing intensities of a spectrum of wavelengths for a given excitation wavelength. In various embodiments, the term fluorescence discussed here may include autofluorescence originating from endogenous fluorphores (e.g., residing in the enamel) and fluorescence originating exogenous fluorophores artificially added (e.g., to a tooth).

Figure 4:
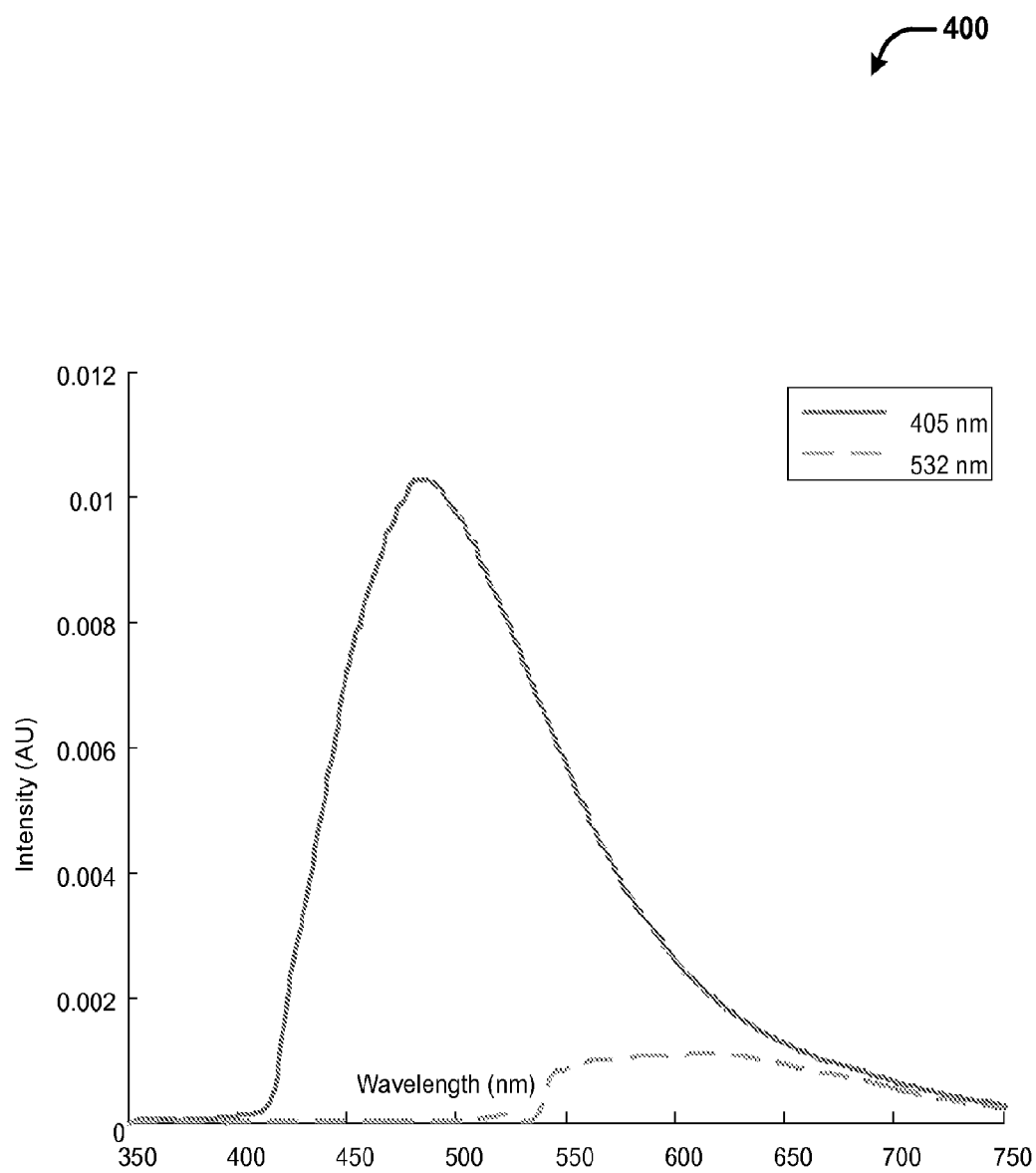
FIG. 4 illustrates example dental AF spectra for 405 nm and 532 nm excitation wavelengths.

In general, fluorescence wavelength shifts as a function of excitation wavelength to longer wavelengths for longer excitation wavelengths on the red-edge of the fluorophore absorption band. The shifted fluorescence bands may represent a unique interaction of the dental fluorophore and the local environment. See, for example, "Red-shifted Fluorescence of Sound Dental Hard Tissue," Zhang, et al., Journal of Biomedical Optics 16(7), 071411 (July 2011), which is hereby incorporated by reference. For example, FIG. 4 illustrates example AF spectra for different excitation wavelengths of 405 nm and 532 nm. As illustrated in this example, the spectrum from the 405 nm excitation shows broad emission centered around 480 nm and gradually tapers off toward the longer wavelengths. The weaker spectrum from the 532 nm excitation is similar in shape but is shifted towards red with the peak fluorescence at around 580 nm. As shown in FIG. 4, the separate, respective AF spectrums may include common and at least partially overlapping ranges of contiguous wavelengths. To obtain separate but common emission spectra for each of two or more excitation wavelengths, the excitation and emission detection associated with each wavelength may be performed separately and possibly sequentially. As also shown in FIG. 4, the range of wavelengths that make up each emission spectrum may be substantially unfiltered (e.g., excluding the excitation wavelength) and include, for example, a range of wavelengths that substantially comprises the visible spectrum from about 390 to about 700 nm.

Referring back to FIG. 3a, spectral information for each of the emission spectrum corresponding to a given excitation wavelength may include an area-under-the-curve value associated with the emission spectrum (e.g., by integrating light intensity with respect to emission wavelength), band shape, peak intensities and the like.

In an embodiment, such spectral information may be used to obtain 306 a value that indicates a relationship between the spectral information for various excitation wavelengths. The value may include ratio, maximum, minimum, mean, median, sum, difference, and any other mathematical relationship. For example, in an embodiment, the value includes a ratio between the integrated area under the emission spectrum curves for two distinct excitation wavelengths (e.g., a 405/532 nm ratio of area under the curve for the example shown in FIG. 4 is approximately 7.66).

Figure 5:
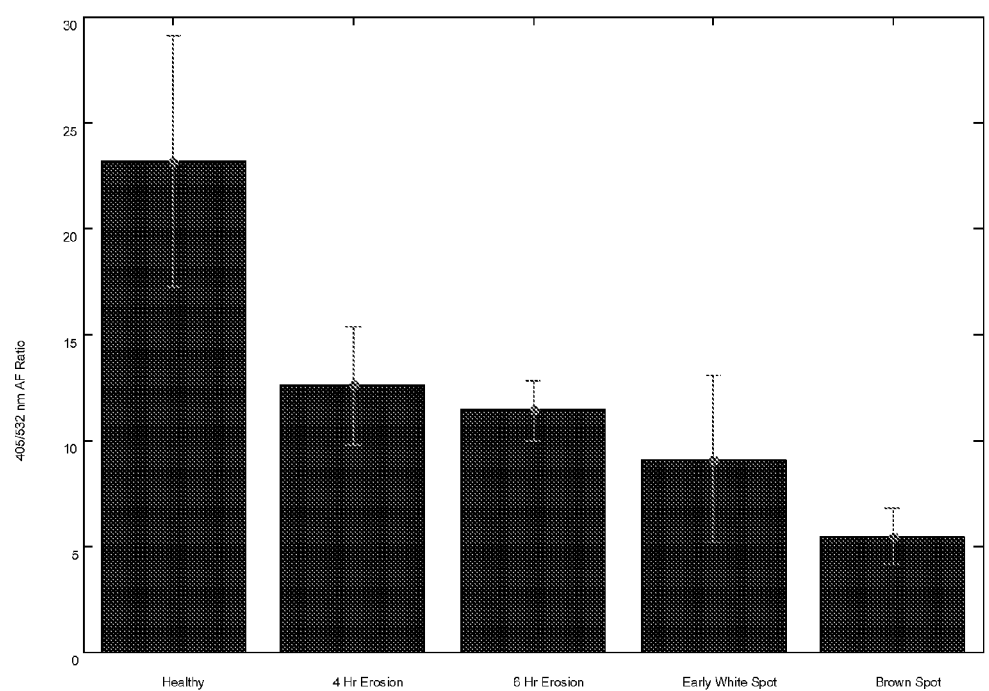
FIG. 5 illustrates an example graph showing a relationship between the 405/532 nm AF ratio and enamel health.

Still referring to FIG. 3a, in an embodiment, the value such as obtained above may be used to determine 308 the dental health (e.g., existence and/or severity of caries or decays) associated with the area in question. For example, a ratio between the integrated spectra for a pair of excitation wavelengths may vary between healthy and defective teeth. FIG. 5 illustrates an example graph showing a relationship between the 405/532 nm AF ratio and enamel health. As illustrated, healthy enamel has the highest ratio, with a trend of decreasing ratio values as severity of lesion (e.g., demineralization) increased. Using a predetermined relationship or trend such as illustrated by FIG. 5, the existence and/or severity of the caries or decays may be determined.

In some embodiments, the dual- or multi-spectral approach allows for an internal calibration to account for changes in topography (e.g., due to distance from the enamel surface to the scanning fiber tip or due to the angle of the enamel surface with respect to the fiber). Since such topology changes are likely to have similar effect on emission spectra of all of the lasers, such effect may be reduced or minimized by taking ratio of the spectra data associated with the lasers.

FIG. 3b illustrates another example process 300B for detecting dental caries or decays, in accordance with an embodiment. In an embodiment, process 300B includes obtaining 310 a first set of laser-induced AF spectral information for two excitation wavelengths for a first area. Such as described in connection with process 300A of FIG. 3a. For example, the set of laser-induced AF spectral information may include the emission spectra information provided by a spectrometer for two excitation wavelengths such as 405 nm and 532 nm. In alternative embodiments, spectral information for more than two distinct excitation wavelengths (e.g., 405 nm, 444 nm and 532 nm) may be obtained. Subsequently, a first ratio of integrated area of AF spectra for the two excitation wavelengths may be calculated based at least in part on the first set of AF spectral information described above. Such calculation may be performed by a computer system such as described in connection with FIG. 1.

Steps 310 and 312 may be repeated to obtain 314 second laser-induced AF spectral information for the two excitation wavelengths for a second area and calculate 316 a second ratio of integrated area of AF spectra for the two excitation wavelengths based on the AF spectral information. The dental health of one of the areas (e.g., second area) may be determined 318 by comparing the first ratio and the second ratio.

As shown in FIG. 5, AF ratios (such as the first ratio and the second ratio described above) are different between healthy and unhealthy enamel. Moreover, AF ratios may also differ from person to person. Therefore, in some cases, it is necessary to establish an intra-specimen standard by repeating steps 310 and 312 across multiple teeth of a patient. For each tooth, an AF ratio is obtained and the percentage change from the lowest ratio to the highest ratio may be used as the diagnostic criteria.

When multiple teeth are scanned, such as by a mouth-guard-like device discussed in connection with FIG. 13, it may be beneficial to separate out data for each tooth, as data recorded from such a scan is not just from one tooth, but from each of the scanned teeth or each tooth condition of caries versus sound across the multiple teeth. To separate this data, frequency analysis may be performed. In the initially recorded data, the AF signal may be modulated by the tooth to tooth spacing distance. On this recorded data, a Fourier analysis may be used to determine the lowest frequency, which can be used to calculate the width of each tooth as well as the spacing between the teeth. A low pass filter such as a simple rectangular or Gaussian filter may be applied to remove the low frequency tooth-to-tooth signal, leaving the higher frequency changes in AF ratio due to presence of carious enamel.

In some embodiments, the multi-laser-induced fluorescence spectroscopy discussed in connection with FIG. 3 may be applied to non-AF spectra. In some embodiments, exogenous fluorescence agents such as fluorescein, methylene blue, and the like may be added to the oral cavity to measure penetration into cracks, decay, fissures, pockets, demineralization, hypoplasia, hyperplasia, biofilm species, plaque, or other disease states. These fluorescence or phosphorescence agents can be excited using any one or more suitable excitement wavelength (e.g., ultra-violet, to visible, to infrared wavelengths). In some embodiments, chromophores, dyes, or pigments to the oral cavity to measure penetration into cracks, decay, fissures, pockets, demineralization, hypoplasia, hyperplasia, biofilm species, plaque, or other disease states. These chromophores can be absorbing and/or scattering in the ultraviolet, to visible, to infrared wavelengths. These agents such as methylene blue may also be photo-sensitizing agents that can be used to kill local bacteria.

In some embodiments, multi-laser-induced fluorescence spectroscopy discussed in connection with FIG. 3 may be performed in conjunction with other scanning and/or imaging activities to increase detection rate. To perform optical diagnosis or therapy, longer dwell time is often required than during wide-field imaging. During the dwell time between image scans (e.g., 3 ms between each imaging frame at 30 Hz), fluorescence spectra on a spot location may be recorded and subsequently analyzed according to the multi-spectral approach discussed above. In this manner, imaging (e.g., using fluorescence and/or visible light) can be performed simultaneously with spot spectral analysis. Subsequently, visual display of the result of such spectroscopic analysis (e.g., locations, types and/or severity of detected caries or decays) may be provided in conjunction with other scanned images and/or on the teeth themselves.

Figure 6A:
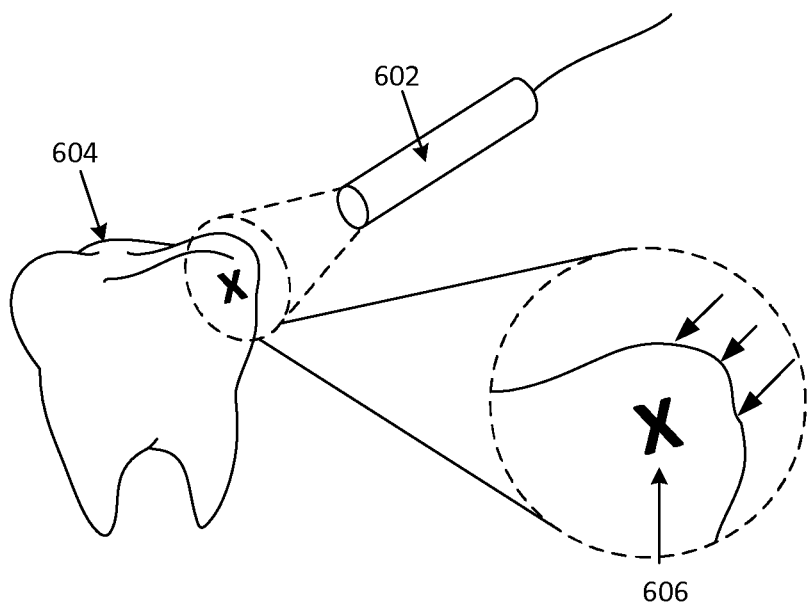
FIGS. 6a-b illustrate examples of such visual indications in accordance with some embodiments.
Figure 6B:
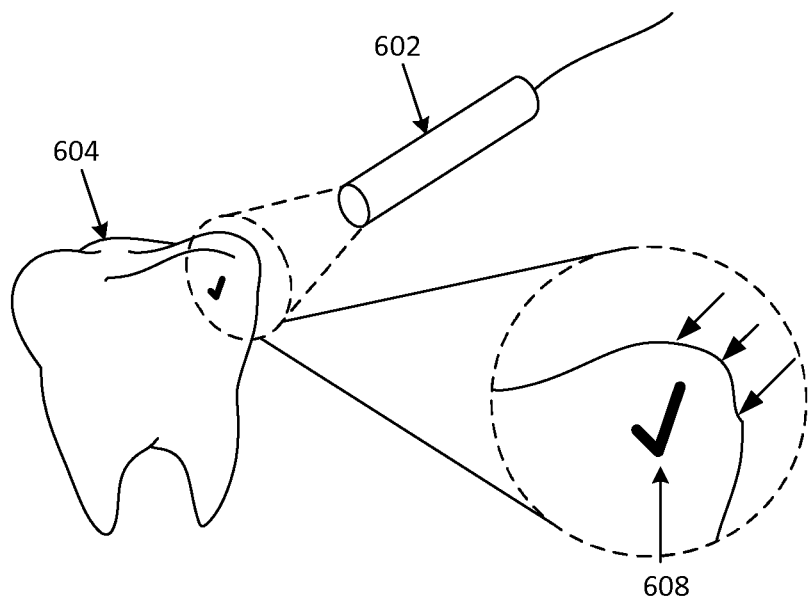

In some embodiments, result of data analysis and/or processing or other indications may be visually projected directly onto a dental region such as the surface of a tooth to aid visual inspection of the dental region, indicate location and/or severity of a dental caries or decay, mode or status of a dental instrument, progress of an examination or procedure and the like. Advantageously, such visual indications may allow a clinician to keep eyes on the teeth and/or procedure at hand (e.g., without pausing to look at a separate display of images or a dental instrument). FIGS. 6a-b illustrate examples of such visual indications in accordance with some embodiments. For example, as shown in FIG. 6a, a probe 602 such as discussed in connection with FIGS. 1 and 2 may be used to project a symbol 606 onto a tooth 604 to indicate the presence of dental decay. Such a display may be based on previous processed AF spectral information (e.g., AF ratio of multi-laser-induced spectra integrals). That is, characteristics of the display may be determined after and responsive to values or results of data detected, processed, or generated by a dental health detection system, such as system 100. As shown in FIG. 6b, a different symbol 608 may be displayed to indicate healthy enamel. In various embodiments, the display may include different colors, patterns and/or other predetermined visual indications that selectively correspond to results of the data analysis and/or processing or other indication. For example, a red dot may be projected onto a particular location of a tooth indicating that caries has been detected on that location. As another example, a green light may be projected onto a tooth to indicate that the tooth is generally healthy, a red light may be indicate the tooth has caries or decay and a blue light may indicate that the tooth requires closer examination.

In various embodiments, such indication may be based on the processing of data recorded in the same or a previous session. For example, the indication may be based on values detected or generated by such processing, such as one or more of input signal values of the detected AF spectra or a generated ratio of such spectra as discussed above. The data may include previously collected dental data such as scanned image data, x-ray data, and the like, as well as data provided by the patient (e.g., patent's medical records), the clinician (e.g., clinician's treatment plan and procedure steps), other dental instrument (e.g., operational status) and the like. In some embodiments, such visual indications may or may not be provided in real time based on signals and/or data collected or processed in real time or nearly contemporaneously.

In various embodiments, visual indications discussed above may be provided by the same or different endoscope or fiber(s) that is used to scan and/or image a dental area. The light source(s) for the visual indications may be the same or different light source(s) than those for scanning, imaging and/or diagnostic purposes. In addition, other indications such as audio indications may be provided in combination with the visual indications to aid the inspection of dental areas.

According to another aspect of the present invention, methods for reducing specular reflection are provided. In the context of image capture, specular reflection occurs when the specular component of light from the illumination source reflects off a surface and directly enters a detector or collection optical fiber which leads to a detector. Since response of a detector to a specular component is typically greater than the response to a diffuse component, such specular reflection may cause portions of images to saturate, obscuring the image information in the affected area.

While the issue with specular reflection is mostly associated with reflectance imaging, it may also occur in fluorescence imaging using SFE. In some cases, some of the illumination wavelength may leak through due to imperfect optical filters and other factors. When a spike of light is collected due to specular reflection, this will cause a spike in the light leakage and show-up in the fluorescence image as specular reflection bleed through. Such phenomenon may be more apparent in fluorescence systems with narrow Stokes shift between excitation and emission wavelengths of the fluorescence.

Figure 7:
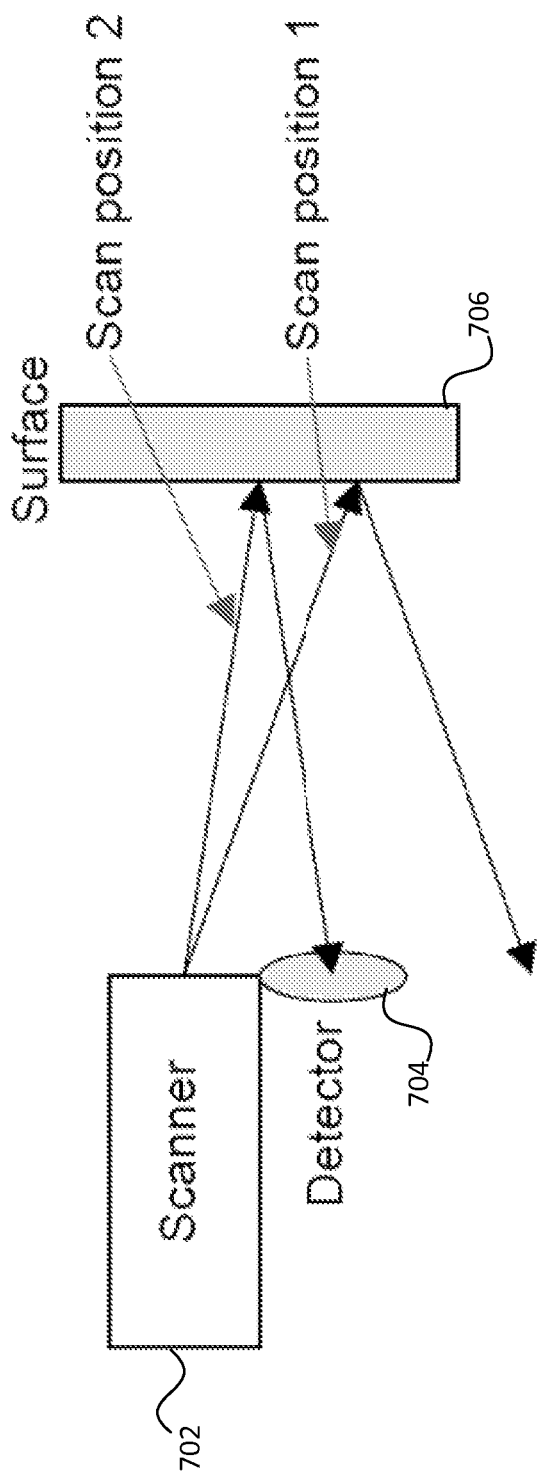
FIG. 7 illustrates an example scanned beam system showing two separate scanned beam positions.

FIG. 7 illustrates an example scanned beam system showing two separate scanned beam positions. In an embodiment, a scanner 702 such as an SFE drives a single fiber to scan in a predetermined pattern to deliver illumination to a surface 706 to be imaged. Light reflected from the surface 706 may be captured by a detector 704 such as described above. While the detector 704 is shown to be near a distal end of the scanner 702 in FIG. 7, in some embodiments, one or more detectors may be located away from the distal end and configured to receive light relayed by collection fibers.

As illustrated in FIG. 7, the scanner may be configured to scan in two positions, scan position 1 and scan position 2 at different times. In scan position 1, the specular component of the reflected signal does not strike the detector 704 so the detector 704 receives only diffuse reflected light (not shown), which may be used to form an image of the scanned area. In scan position 2 the specular component of the reflected signal does strike the detector 704. In this position the detector 704 receives both the diffuse and specular components of the reflected light. Since response from a specular component is typically greater than that from a diffuse component, the detector's response in scan position 2 may be greater than in scan position 1, creating a bright spot in the scanned image and obscuring the true image data (e.g., from diffuse component).

In some embodiments, specular component of reflected light may be narrowly focused and may strike only a single collection fiber at a time during scanning while the other collection fibers may receive only the diffuse component of reflected light. However, when light from all fibers are combined and imaged onto detectors, the specular component from any of the fibers may be sufficient to cause saturation, especially for highly sensitive detectors such as PMTs.

Figure 8:
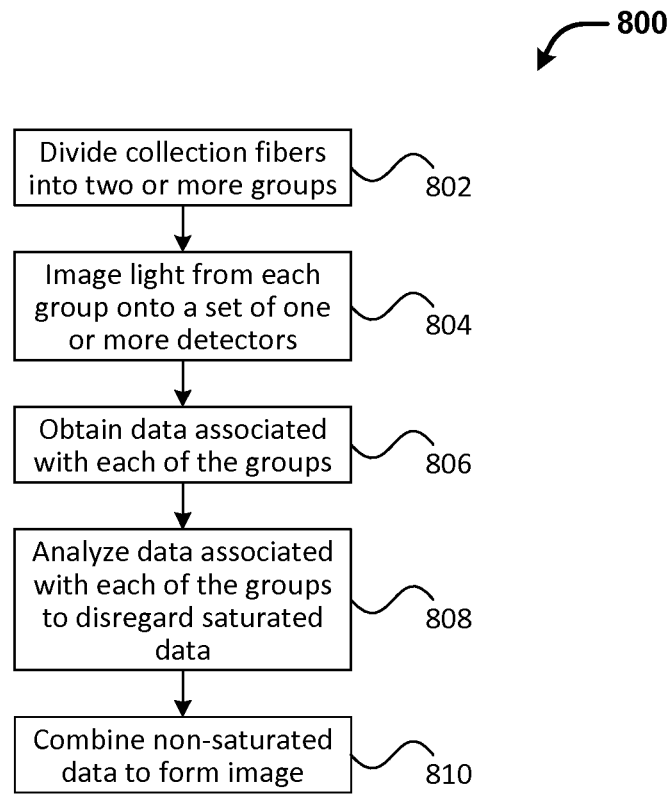
FIG. 8 illustrates a process for reducing specular component of reflected light to improve quality of images, in accordance with an embodiment.

FIG. 8 illustrates a process 800 for reducing specular component of reflected light to improve quality of images, in accordance with an embodiment. In some embodiments, aspects of process 800 may be implemented by components of a dental health detection system such as discussed in connection with FIG. 1.

In an embodiment, process 800 includes dividing 802 light collection or return fibers into two or more groups. As discussed above, multiple collection fibers are typically used to collect backscattered light during a scanning process. Such collection fibers may be divided into two or more groups based, for example, on the relative position and/or orientation of the fibers. For example, the fibers may be divided into four quadrants based on their positions relative to the scanning or illumination fiber.

For each group, light from all fibers in the group may be combined and imaged 804 onto a set of photodetectors (such as described above). In some embodiments, the combined light may be first separated by wavelength or color (e.g., by using filters) before being received by the photodetectors. For example, the set of photodetectors may include multiple RGB detectors, each configured to detect light within a specific range of wavelengths.

Next, optical data associated with each group (and hence the associated set of detectors) may be obtained 806. Such data may indicate an energy level associated with detected light. In some embodiments, the data may include analog signals such as produced by an analog photodetector. In other embodiments, the data may also include digital data. For example, such digital data may be provided by a digital photodetector or converted from analog signals produced by an analog photodetector.

The data associated with each group may be analyzed 808 to determine whether there is saturation and if so, the saturated data may be disregarded (e.g., via filter or threshold). Disregarded data may not be used in forming the final image. Saturation may be considered present when an energy level exceeds such a threshold value. In some embodiments, such threshold values may be determined based on contemporaneously or near-contemporaneously acquired data. For example, if one set of detectors produce signals much greater than the other remaining set of detectors, then data associated with the one set of detectors, then the sampled data from the one set of detectors may be discarded from the signal data with the assumption that the one set of detectors sampled specular reflection. In some other embodiments, the threshold values may be based on past measurement signal values (e.g., previously acceptable levels of optical signal from the previously acquired image frame). In yet other embodiments, the threshold values may be set by a manufacturer or specified by a user. In various embodiments, the methods discussed herein may apply to both analog signals and digital data. In some cases, it may be determined that specular reflection may affect more than one groups of detectors. In such cases, data associated with some or all of the covered sets of detectors may be disregarded. In some embodiments, data associated with the covered sets of detectors may be modified instead of being disregarded.

Finally, in an embodiment, the data with the remaining groups, considered unsaturated, may be combined 910 (e.g., averaged) to form an image.

Variations of the above described process are also considered. For example, in an alternative embodiment, a signal comparator may be used to remove spikes in the signal from detectors on the same color (wavelength) channel. For example, two or more detector outputs for the red color channel may be compared in terms of the magnitude and/or duration of the signal. If a spike is detected, the spike may be removed from the signal. In some embodiments, similar electronic filtering techniques can be employed to eliminate spikes of noise from electronic circuits or other hardware components.

In some embodiments, specular reflection may be reduced based on knowledge of the orientation of the scanned laser beam, the object being imaged and the like. For example, by knowing the instantaneous position of the scanned fiber tip and the resulting scanned illumination beam and the general orientation of the object or tissue being imaged with respect to the distal end of the probe, the direction, position, and extent of the specularly reflected light can be estimated. Such estimation may be used to filter out or remove signals or data derived from certain detectors.

According to another aspect of the present invention, methods for facilitating sterility and hygiene during an intraoral procedure (or other types of procedures) are provided. In particular, disposable sleeves may be used to cover a distal portion of an endoscope or a probe (such as an SFE) to preserve hygiene while the endoscope is being used. Such sleeves may be disposable to maintain the cleanliness of the endoscope and/or to facilitate the (sometimes frequent) reuse of the endoscope between different subjects. In addition, such sleeves may be configured to provide various endoscopic functions as discussed below.

Figure 9A:
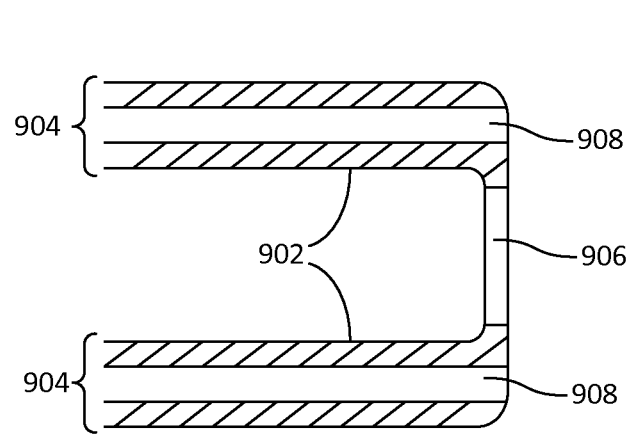
FIGS. 9a-c illustrate examples of sleeves, in accordance with some embodiments.
Figure 9B:
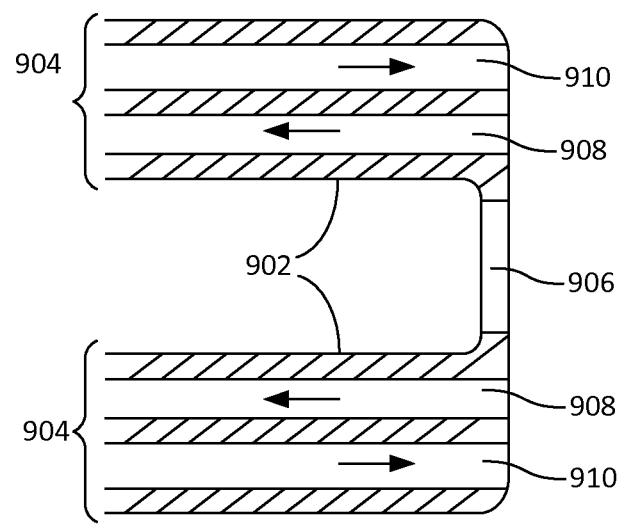
Figure 9C:
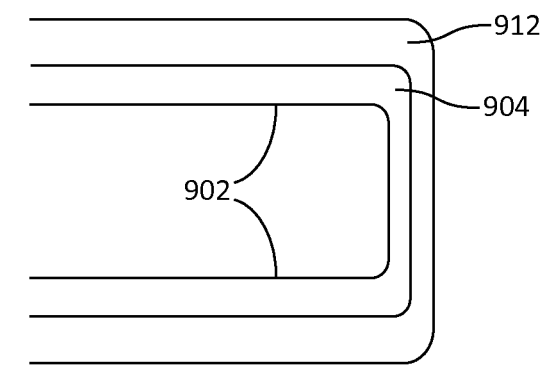

FIGS. 9a-c illustrate some examples of the sleeves described above, in accordance with some embodiments. In each example, a sleeve 904 is shown as fitted over a distal end of an endoscope or probe 902. The sleeve may include a window 906 to allow illumination for illumination and/or collection of light. In addition, the sleeve 904 may include any number (e.g., one, two or more) of channels 908. For example, the sleeve illustrated in FIG. 9a includes two channels whereas the sleeve illustrated in FIG. 9b includes four channels. Such channels may act as conduits for fluid (e.g., gas or liquid) and/or optical signals. The channels may be open (e.g., for gas and/or liquid) or solid (e.g., to carry light signals). In some embodiments, the channels may be connected to a base station with fluid pumps, detectors, sample storage and the like. For example, the channels 908 in FIGS. 9a and b may include one or more optical fibers to collect light reflected from a scanned surface and/or imparting higher optical energies onto an area such as a surface of a tooth. Additionally, channels 910 in FIG. 9b may be configured to provide air, such as may be necessary to dry up a dental area during a dental procedure. In some other embodiments, the channels may be used to provide spray or other liquid to an area or collect fluid (e.g., gas, liquid) or tissue (e.g., during a biopsy procedure) from the area.

Other variations are also considered. For example, in an embodiment, a sleeve includes one channel for carrying optical signals for the left eye of a user and another channel carrying optical signals for the right eye of the user for stereo viewing. As another example, a sleeve includes one or more channels for illumination and another set of channels for collection of scanned light signals. In some embodiments, a channel may be configured to perform only one function such as light collection. In other embodiments, the same channel may be used for multiple purposes such as spraying liquid and providing air.

Advantageously, the sleeves configured with channels provide a space-efficient way of providing a variety of functionalities (e.g., air, liquid, light delivery and/or collection) that would otherwise require extra lines and/or equipment. The reduction or elimination of such extra equipment may be desirable in a small or restricted space, such as inside a person's mouth.

In some embodiments, such as illustrated in FIG. 9c, multiple sleeves 904 and 912, each with or without its own set of channels, may be applied to the distal end of the same endoscope or probe 902. For example, as illustrated, the distal end of the endoscope 902 may be covered by an inner sleeve 904 which may in turn be covered by an outer sleeve 912. The sleeve 904 may be used to cover an illumination scanning fiber in the endoscope whereas sleeve 912 may be used to include collection fibers include in one or more channels.

Figure 10:
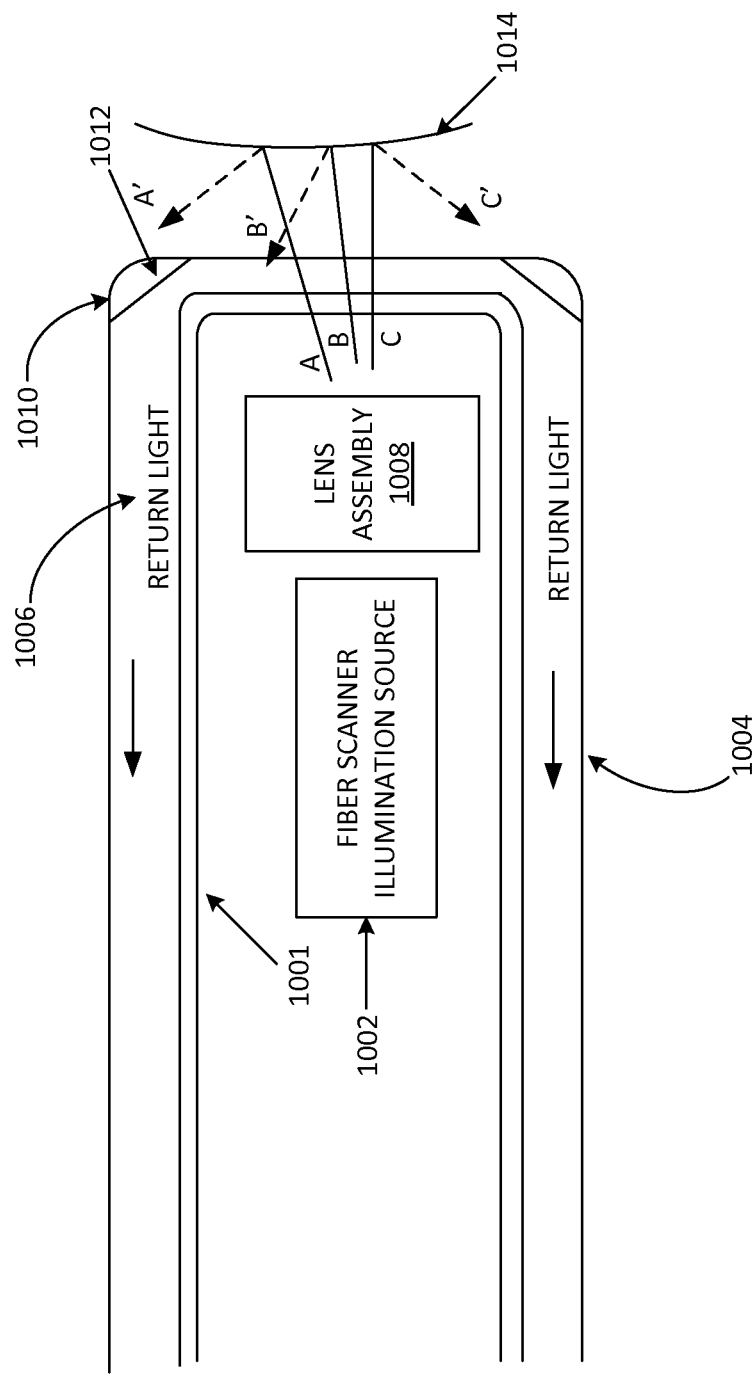
FIG. 10 illustrates an example sleeve that may be used in conjunction with an SFE, in accordance with an embodiment.

FIG. 10 illustrates an example sleeve that may be used in conjunction with an SFE, in accordance with an embodiment. Such an SFE may be used in a dental procedure for imaging, diagnostic or therapeutic purposes. In this example, a sleeve 1004 similar to those described above may be used to cover a distal portion of an SFE comprising a housing 1001 that contains a fiber scanner illumination 1002 used to drive a fiber to scan in predetermined patterns and a lens assembly 1008 such as described in connection with FIG. 2. During scanning, light from the fiber scanner illumination 1002 may go through the lens assembly 1008 and reach an area of interest 1014. As illustrated, scanned laser beam A, B and C are illustrated in the figure with A', B' (not shown) and C' being reflection of A, B and C, respectively.

In this example, the sleeve 1004 includes two or more optical channels 1006. The channels may be configured to collect backscattered light, reject specular reflection and/or perform other optical functions. In general, various methods may be used to improve light collection efficiency and image quality. For example, each channel 1006 may include a total internal reflection corner 1010 with a low-refractive-index air gap 1012 to facilitate efficient collection of backscattered light and/or to reduce or eliminate specular reflection. In some embodiments, the optical fiber ends and/or light conduits may be angled to capture light at high numeric aperture. In some embodiments, hardware (e.g., comparator circuits) and/or software components may be used to remove specular reflection (e.g., spikes in signal) using methods such as discussed in connection with FIG. 8.

In some embodiment, the sleeve may include one or more channels to carry out functionalities specific to dental diagnosis or therapy. For example, the sleeve may include one or more air channels (not shown) for spraying or otherwise providing fluid (e.g., liquids) and/or optionally for drying teeth. For another example, the sleeve may include one or more channels configured to support dental accessories.

In some embodiments, the probe such as an SFE may or may not include return optical fibers for collecting return light. Typically, the probe is reusable across patients. In contrast, the sleeve that covers the probe is typically disposable (e.g., after single use). The sleeve may include a sheathing with one, two or more channels such as described above. Such channels may include optical signal conduit (e.g., optical fiber), accessory channels (used to carry accessories), fluid (e.g., gas, liquid) or return light channels and the like. In addition, the sleeve may include procedure-dependent sizing and/or tip bending. The sleeve may also include one or more windows to allow through the illumination from the probe. In some embodiments, such window may be angled or otherwise configured to reduce laser reflection.

In various embodiments, the sleeve may be symmetric or asymmetric along a central axis (e.g., illumination fiber) of the probe that the sleeve covers. In some embodiments, an asymmetric sleeve may be used to fit an asymmetrically-shaped probe. In some other embodiments, asymmetric sleeves may be used to provide different numbers and/or types of channels on each side. For example, in an embodiment, a sleeve may include one channel on one side and two channels on the other side of the central axis. As another example, the sleeve may include a bigger air channel on one side and a thinner optical fiber channel on the other. In yet other embodiments, the asymmetric shape of the sleeve may be used to tip bending of the probe, or to provide other functionalities.

As discussed above, in some embodiments, a window may be located at the distal portion of the sleeve to allow light from the probe to pass through. The window may be made from a rigid clear material such as hard clear plastic, such as acrylic (Poly(methyl methacrylate)), or any other suitable material. The rest of the sleeve may be made from a more flexible material such as soft polyurethane and may be joined with the window near the edge the window. Alternatively, the window and the rest of the sleeve may be made from the same material, such as low-density polyethylene (LDPE). In various embodiments, the material(s) used for some or all portions of the sleeve may have minimal autofluorescence so as to avoid interference with the illumination and/or collection of fluorescence. For example, a material with such minimal autofluorescence would be a very thin clear polymer like LDPE low-density polyethylene that is highly flexible. Alternatively, a system, such as the computer/controller/detector system 108 discussed in connection with FIG. 1, can acquire baseline autofluorescence spectral measures during an initialization step which is then used to subtract from the measured autofluorescence in a post processing step.

In an embodiment, to put the sleeve on the probe (e.g., SFE), the user positions the distal end of the capsule against or close to the window of the sleeve, hold a distal portion of the sleeve (with probe) in place, and roll out the rest of the sleeve toward the proximate end of the probe. The portion of the sleeve that is not yet rolled out may be rolled up to form a hoop with a relatively large diameter so that the portion may be unrolled relatively quickly. In some embodiments, the sleeve may extend in length (e.g., one meter) to cover a portion of a shaft connected to the proximal end of the probe, as necessary, to maintain biological safety. In some embodiments, the sleeve may be heat-shrunk after being applied to a probe to ensure a tighter fit over the probe and/or shaft. In some embodiments, one or more channels (such as air channel) may be attached to the outer surface of the sleeve after the sleeve is fitted over the probe. For example, an air channel may be attached to the sleeve after it is put on via a rail. Such a rail may be a part of the sleeve or attached to the sleeve separately.

According to another aspect of the present invention, screening devices specifically designed for dental screening are provided. FIGS. 11-15 illustrate various embodiments of a screening device used for screening dental caries such as according to the laser induced fluorescence spectroscopy described above. Such devices may be used to provide scanned light or fixed illumination and to detect backscattered or fluorescent light as described above. In some embodiments, the screen device may be designed to interrogate specific dental regions or the entire mouth of a child or an adult. In some embodiments, the screening device may be used by a dental practitioner or a person without any dental training (e.g., a parent). In addition, the device may be used with other optical measurement and imaging modalities, such as Raman spectroscopies, Optical Coherence Tomography (OCT), fluorescence lifetime measurement, UV-Visible-NIR optical imaging in reflectance and transmission and the like.

Figure 11A:
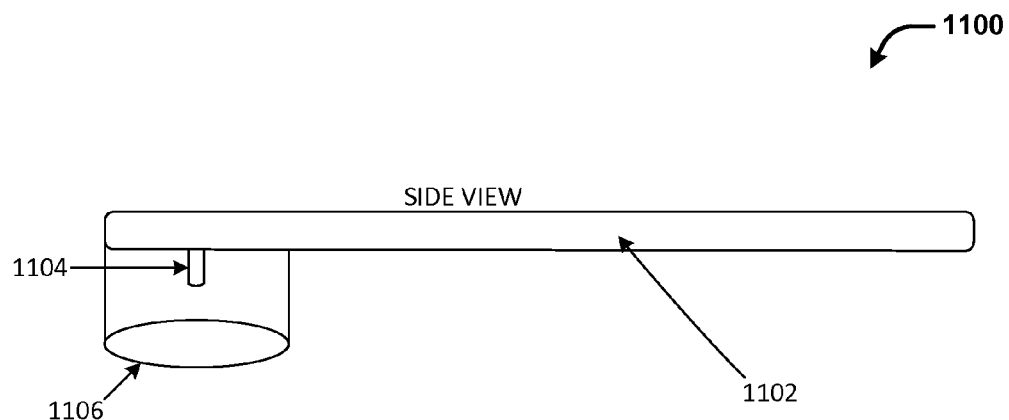
FIGS. 11a-b illustrates side and top-down view of a tooth-brush like screening device, in accordance with an embodiment.
Figure 11B:
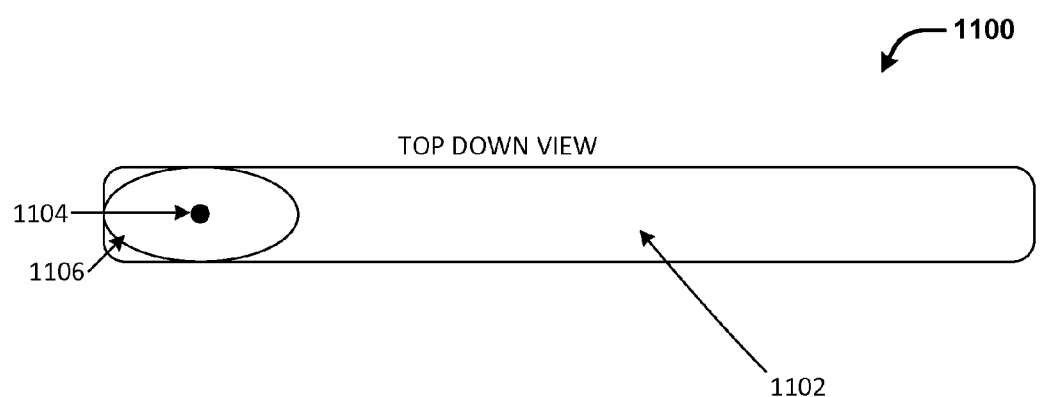

FIGS. 11a-b illustrates side and top-down view of a tooth-brush like screening device 1100, in accordance with an embodiment. When in use, the device 1100 may be held by a user by the handle 1102 of the device 1100 like a toothbrush, with the head of the device 1100 over a tooth. The head of the device may include a distal end of an optical bundle 1104 and a curtain 1106. The optical bundle 1104 may include a bundle of optical fibers comprising a central illuminating fiber for delivering (e.g., scanned or non-scanned) light on a tooth and return fibers for capture the emitted light such as AF. The collected light may be sent along the collection fibers (e.g., hidden inside the handle 1102) to the base station for processing and analysis. In some embodiments, the curtain 1106 may be used as a standoff as well as a hood to minimize ambient light. The curtain may be of any suitable shape (e.g., circular) or made with any suitable material (e.g., rubber).

Figure 12A:
FIGS. 12a-c illustrate example tooth-brush like screening devices, in accordance with some embodiments.
Figure 12B:
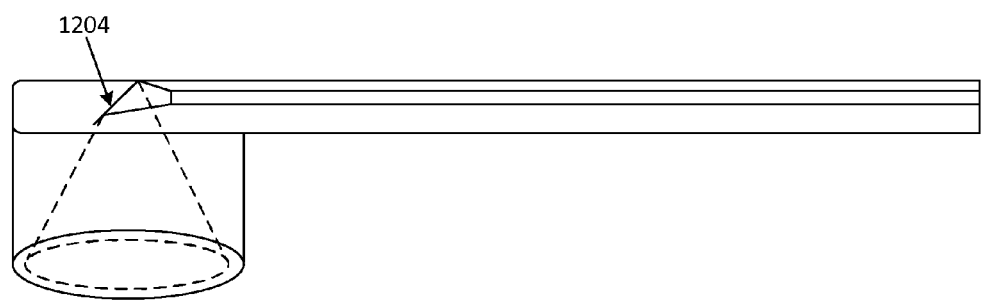
Figure 12C:
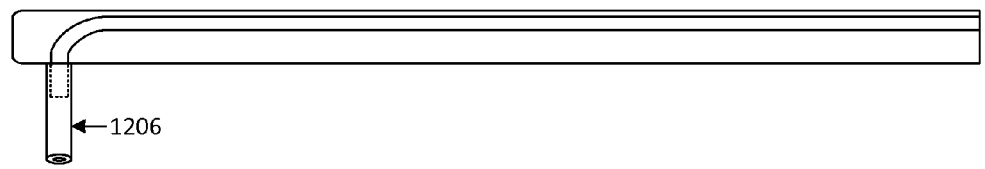

FIGS. 12a-c illustrate example tooth-brush like screening devices, in accordance with some embodiments. In an embodiment, such as illustrated in FIG. 12a, a distal end 1202 of the optical bundle may be bent downward toward the tooth to be scanned. In alternative embodiment, such as illustrated in FIG. 12b, a mirror 1204 or a similar optical device may be used to redirect light from the optical bundle so that the tip of the optical bundle does not need to be bent.

Various methods may be used to lower the cost of the screening device. In an embodiment, the scanning may be performed manually rather than automatically (e.g., driven by a piezoelectric actuator), by manually moving the illumination fiber, by manipulating the mirror or by other means. In another embodiment, the cost may be further lowered by having a fixed fiber/mirror setup and having a user manually move the device over the tooth to scan across it (e.g., as if brushing the tooth). In yet another embodiment, such as illustrated in FIG. 12c, a distal end of the optical bundle of the device may interface (and hence become elongated) with a stiffened tip 1206, which may act as a standoff. In such an embodiment, the user may scan the tooth by placing the stiffened tip against a tooth and manually move the tip along the tooth.

Figure 13:
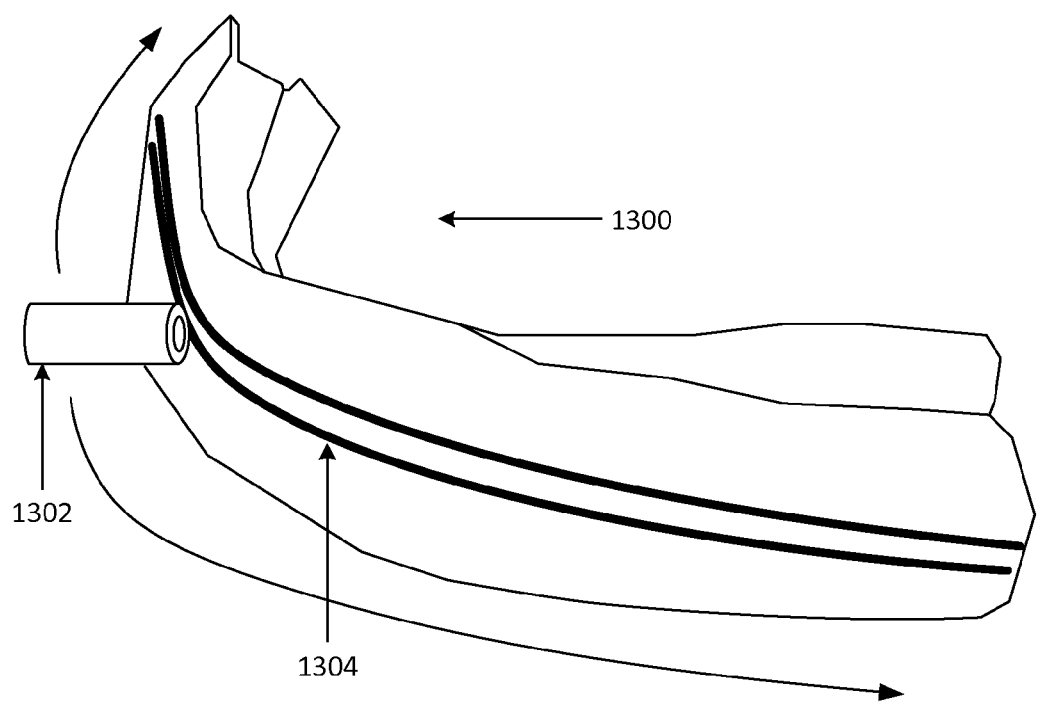
FIG. 13 illustrates a mouthguard-like screening device, in accordance with an embodiment.

FIG. 13 illustrates a mouthguard-like screening device 1300, in accordance with an embodiment. When in use, such a device 1300 may be worn over the front teeth of a patient. An optical bundle 1302 may be detachably coupled to a track 1304 that runs along the length of the device 1300 along the front teeth. The optical bundle 1302 may be configured to scan along the track 1304 manually or automatically to obtain signals or data (e.g., emitted AF) for further analysis and processing (e.g., at the base station). In another embodiment, multiple fibers and detectors may be embedded (e.g., evenly) along the length of the mouthguard to allow for simultaneous acquisition of signals from multiple teeth. In such an embodiment, the device may be connected to a separate base station where the data can be processed and displayed to a user. In some embodiment, the optical bundle may be detached from the mouthguard and reused between patients, whereas the mouthguard may be disposable and/or customizable to each patient.

Figure 14:
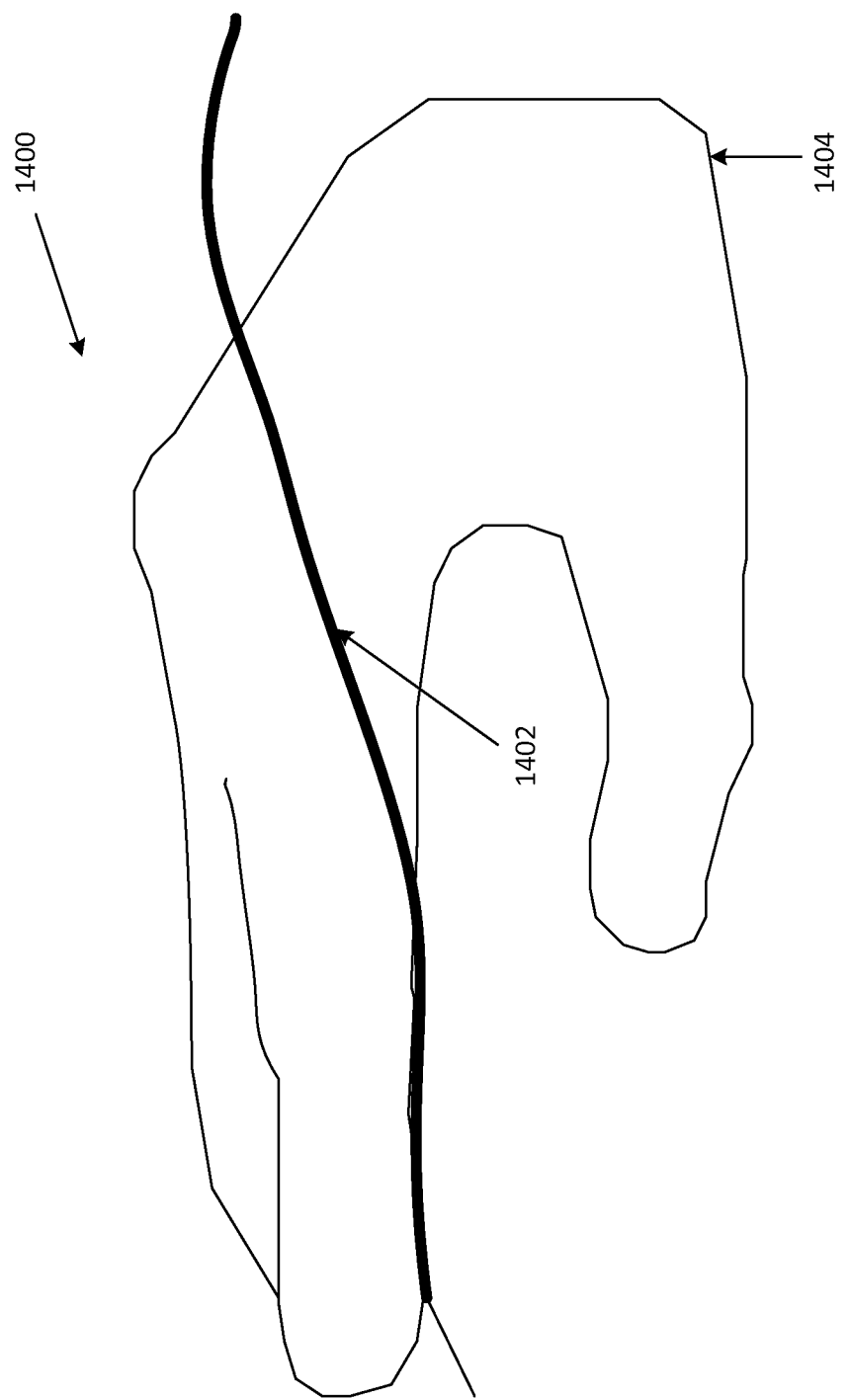
FIG. 14 illustrates a glove-like screening device, in accordance with an embodiment.

FIG. 14 illustrates a glove-like screening device 1400, in accordance with an embodiment. In an embodiment, such a device may be used to interrogate the front incisors of a child. When in use, such a device 1400 may be worn over a hand of a person performing the screening. An optical bundle 1402 (e.g., comprising one central illuminating fiber and a ring of return fibers) may be attached to a standard examination glove 1404. For example, the optical bundle may be attached along a portion of the bottom of a finger (e.g., index finger).

In an embodiment, a user performs dental screening by putting on the glove-like device on a hand and scanning a distal portion of the optical bundle across a tooth by moving the finger to which the optical bundle is attached to. The distal portion of the optical bundle may or may not touch the tooth during such scanning Additionally, a mirror, prism, or lens may be placed near the distal portion of the fiber bundle to manipulate the direction of the light so that the light may be forward looking, side looking, or in-between. In an embodiment, the user manually wipes the device across the surface of a tooth or teeth to interrogate various regions thereof. In some embodiments, some or all components of the device may be disposable. For example, the glove 1404 may be disposable and the optical bundle 1402 may be detachable from the base station and disposable. Other embodiments are also contemplated. For example, more than one optical bundles may be attached to one or more fingers of the glove to enable simultaneous scanning of multiple teeth or sensing in transmission rather than in reflection mode. Alternatively, the narrow rigid tip of the bundle may stick out from the glove and can be inserted into crevices within a tooth, between teeth, or between the teeth and gums to measure and image below the gum line.

FIGS. 15*a-c* illustrate lollipop-like screening devices 1500, in accordance with some embodiments. As shown in FIG. 15*a*, the device 1500 may be used inside a mouth 1501 to interrogate the lingual side of the front teeth such as 1508 and 1510.

FIG. 15*b* shows a side view of an embodiment of the device 1500. The device 1500 includes a spherical head 1504 with a concave mirror 1506 on a distal end. An optical bundle 1502 (e.g., driven by a piezoelectric actuator) is threaded through the stem of the device to provide light towards the mirror 1506, which reflects the light to the back-side of one or more upper 1508 or lower teeth 1510. In one embodiment, this stem may be dimensioned with a width approximately three times the size of its height, so as to permit both the threading of an optical bundle 1502 therethrough and the manual grasp and manipulation by the user of the overall device 1500. Imaging may also be performed by operating the fiber bundle as it is used by the SFE or an elliptical annulus of scanned light may be more appropriate. In an embodiment, excitation laser of varying wavelengths may be scanned across the teeth via reflection on mirror 1506, and the emitted AF may be collected by the optical bundle via reflections from the mirror 1506 and sent back to the base station for processing and analysis such as described in connection with FIG. 3. In the example annular scan, the upper teeth can be scanned in one direction (e.g. right-to-left) while the lower teeth could be scanned in the opposite direction (left-to-right). A lollipop head 1504 may be made from a clear material (e.g., polymer) which allows for light to pass through, including through one or more of above, below, and to the side of the stem.

FIG. 15*c* shows another embodiment of the lollipop-like device 1500. In this embodiment, the head 1504 of the device resembles a flat cylindrical disk rather than a sphere as shown in FIG. 15*b*. In various embodiments, the head of the device may take any other shape. In some embodiments, one or more of the top side, bottom side, and circumferential sides of the head of the device may be rounded. In one embodiment, a planar top side and or bottom side of the head of the device may be constructed to form a reflective plane that directs and light to and from the lingual sides of the teeth and the mirror 1506. In some embodiments, at least a portion of the head of the device may be covered with favored candy facilitate appeal to children. For example, the top side and bottom side of the device, through which diagnostic light does not substantially pass, may be covered with a flavored candy. In some embodiments, a disposable sleeve such as described above may be used to cover the head and optionally a portion of the optical bundle to maintain sanity. In some other embodiments, the head of device may be wiped clean or otherwise sanitized between uses. In yet other embodiments, the device may be detachable from the base station and disposable.

In various embodiments, the screening devices such as discussed above may be used to detect dental caries or decay in various regions of the teeth. For example, glove-like device discussed in connection with FIG. 14 may be well-suited for interrogating the front incisors and the lollipop-like device discussed in connection with FIG. 15 may be well-suited for the lingual side of the front teeth. The mouthguard-like device discussed in connection with FIG. 13 may be well-suited for interrogating the front of the teeth whereas the toothbrush-like device discussed in connection with FIGS. 15-16 may be used on any area of any tooth. In some cases, devices particularly designed to screen the front teeth may be particularly useful in early detection of dental caries since dental caries typically first manifests itself on the smooth front surfaces of the central incisors.

Figure 16A:
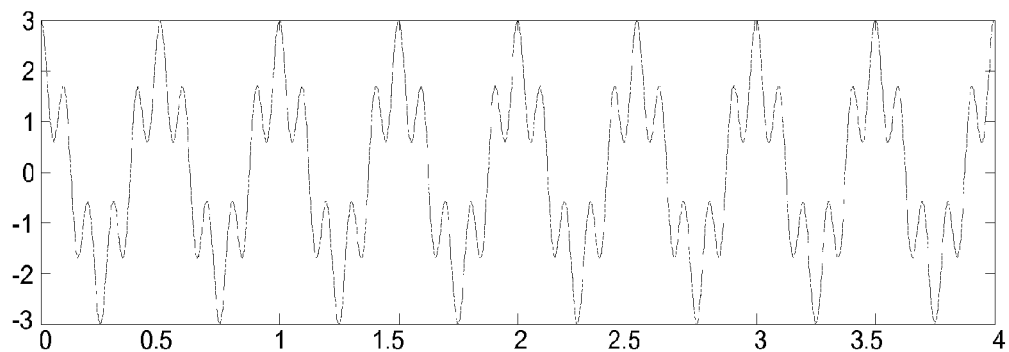
FIG. 16a illustrates an example multi-frequency signal from a mouth-wide scan, in accordance with an embodiment.
Figure 16B:
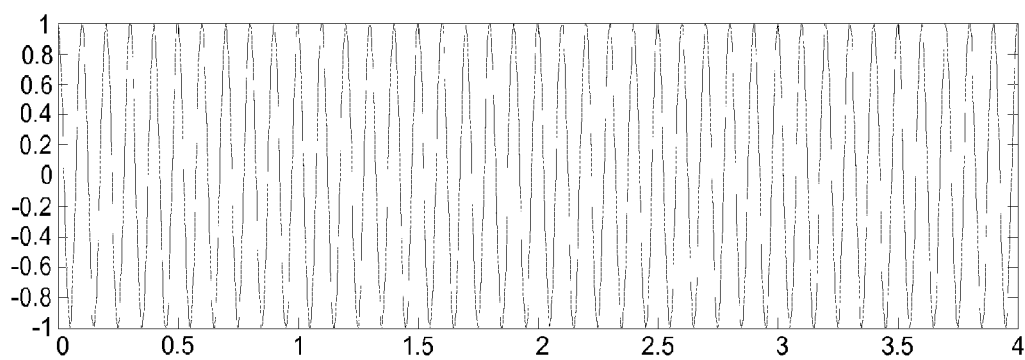
FIG. 16b illustrates an example signal from a mouth-wide scan with the low frequency component filtered out, in accordance with an embodiment.

For embodiments of the screen devices such as the mouthguard or lollipop-like device, a scan (e.g. continuous sampling) across the front of the mouth may be performed. Since the recorded data is not from just one tooth, but from multiple teeth, it is important to be able to distinguish between individual teeth and regions that generate signal. To do so, frequency analysis can be performed. The AF signal from a sweep across multiple teeth will be a multiple frequency signal. In other words, multiple frequency components are superpositioned onto each other to form a waveform with multiple frequency bands. FIG. 16*a* illustrates an example multi-frequency signal as a result of a mouth-wide scan, in accordance with an embodiment. As illustrated, the signal has a large amplitude low frequency component and a small amplitude higher frequency component. The slowly varying component of the signal may be due to the tooth-to-tooth spacing, while the higher frequency component may be due to changes in enamel health within each tooth (e.g., intra-tooth variation due to caries). To remove the tooth-to-tooth low frequency signal from the intra-tooth signal, Fourier analysis may be performed. The Fourier analysis may be used to determine the lowest frequency, which gives information on the width of each tooth. Then, a low pass filter such as a rectangular or Gaussian filter can be applied to remove the low frequency tooth-to-tooth signal. What remains after the filtering will be the higher frequency signal which corresponds to changes in AF ratio due to changes in enamel health (i.e. healthy and carious enamel). FIG. 16*b* shows the same signal as FIG. 16*a* but with the low frequency component filtered out as discussed above.

In some cases, the oscillations in the signal may be due to changes in the enamel health for all teeth scanned, with high values being healthy enamel and low values being demineralized enamel. The range of values across all teeth scanned can give a measure of the health of the hard tissues scanned and even the gums of the patient in a single value. These values can be combined with patient history data, such as past measures, diet, and habits to develop a risk assessment for the caries or gum diseases in the future. Alternatively individual teeth measures can also be separated out from these data and identified with individual measures of health. This procedure assumes the two or more wavelength spectral measurements are made more rapidly than the scan speed across the teeth and/or gums. In addition multiple passes of the scan can be made and the measured spectral responses can be averaged over time, assuming that the repeated laser light scanning covers the same regions of the mouth, teeth, and/or gums.

EXAMPLE

Dental autofluorescence (AF) is based on the presence of endogenous fluorophores residing in the enamel and has been shown depend on excitation wavelengths. In some cases, dental AF behaves as a fluorophore in a rigid solvent environment, and is therefore dependent on the fluorophore/solvent microenvironment. This leads to emission shifts to longer wavelengths for longer excitation wavelengths on the red-edge of the fluorophore absorption band.

In an example described below, a simple and robust AF ratio method was developed to discriminate between sound enamel and different stages of early stage caries lesions. See also, "Optical Measure of Enamel Health," Zhang, et al., 2012 IEEE Global Humanitarian Technology Conference, which is hereby incorporated by reference. Quantitative fluorescence measurements of dental specimens were obtained using 405 nm and 532 nm laser excitation. Fluorescence from sound and early stage natural lesions was obtained and the two fluorescence spectra were analyzed. Toward this, laser-induced autofluorescence spectra were measured from sound and demineralized regions on 18 extracted human teeth. The ratio of the integrated area of the fluorescence spectra from the emission curves between 405 nm and 532 nm excitation lasers were used to develop the reference standard.

The example used extracted human molars and premolars (n=10) with sound and early stage natural caries regions. The teeth specimens were classified using the diagnostic criteria shown in Table 1. All regions with visual signs of early stage caries were noted.

TABLE 1

Criteria for clinical enamel classification

| Category | Clinical Criteria |
| --- | --- |
| Sound | Normal texture of enamel |
| Early White Spot | Opaque or slightly opaque, with loss of luster and rough, intact surface. |
| | Typically located in region of tooth with high percentage of lesion development (e.g. interproximal contact point) |
| Brown Spot | Opaque, with loss of luster and rough, intact surface. Coloration of lesion, typically surrounded by white spot lesion |

The teeth were cleaned and fixed in formalin (10% neutral pH formalin, Sigma-Aldrich, St. Louis, Mo.), the specimens were then stored in a 0.1% thymol (Sigma-Aldrich, St. Louis, Mo.) solution at room temperature. An additional (n=8) extracted human molars and premolars were used to induce artificial erosions. To create artificial erosions, specimens with no clinically detectable natural lesions were used. Acid resistant nail varnish was applied to the enamel, leaving a window. They were then submerged in an acetic acid solution of pH 3 for four and six hours. Table 2 lists the details of the specimen samples used in the study.

TABLE 2

Specimen categories and sample size used.

| Category | Sample Size |
| --- | --- |
| Early Stage White Spot | 7 |
| Brown Spot | 3 |
| Artificial Erosion (4 hour) | 4 |
| Artificial Erosion (6 hour) | 4 |
| Total | 18 |

In preparation for creating artificial erosions, each tooth was removed from the 0.1% thymol solution and rinsed with deionized water and lightly dried with absorbing paper towelettes. Then, acid resistant varnish was applied over each tooth while leaving a small window (approximately 4×10 mm) of exposed enamel on the lingual or buccal side. The prepared specimens were then placed in a custom made circulating acid bath container.

Eight specimens with lingual or buccal surface windows were created. Prepared specimens were placed in a plastic container and submerged in an acetic acid solution of pH 3. A rotating stir bar (600 rotations per minute) was used to minimize areas of stagnant solution around the exposed enamel. Submersion times of four (n=4) and six hours (n=4) were used to create erosions of varying severity. After the specimens were removed from the acid solution, deionized water was used to remove and remaining acid. Then, acetone was applied onto a cotton swab, which was then used to remove the varnish.

Figure 17:
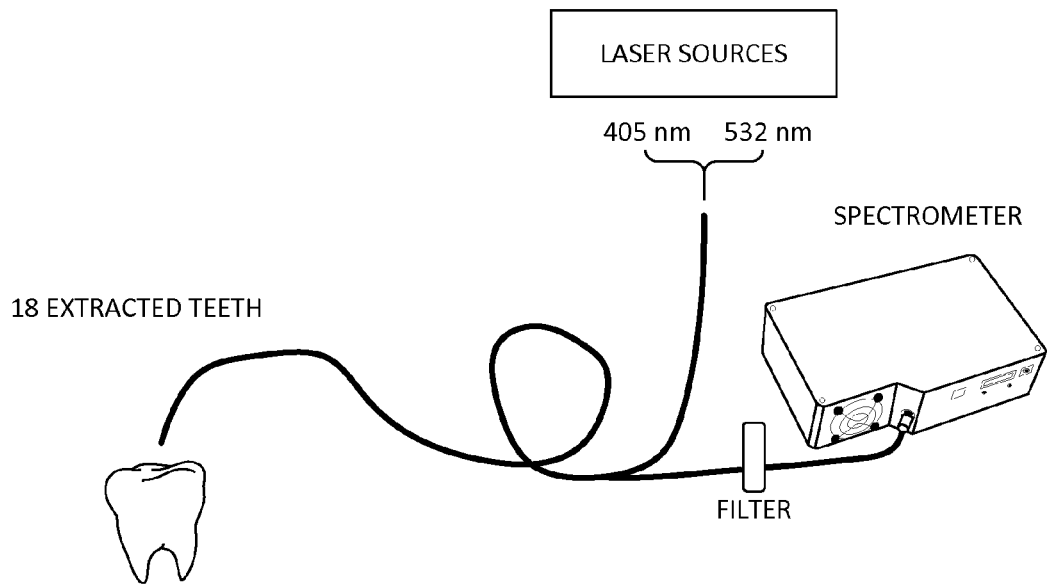
FIG. 17 illustrates a laser-induced autofluorescence spectroscopy system developed for early stage caries discrimination, in accordance with an embodiment.

A laser-induced autofluorescence spectroscopy system was developed for early stage caries discrimination is shown in FIG. 17. The system uses a coupled diode laser module (such as FTEC2 developed by Blue Sky Research of Milpitas, Calif.) containing a 405-nm laser diode (such as NDV4313 developed by Nichia Corp. of Tokushima, Japan), and a 532-nm fiber coupled diode laser module (such as FTEC2). Emission spectra were measured using a commercially available thermoelectrically cooled CCD array based miniature fiber optic spectrometer (such as QE65000 FL developed by Ocean Optics Inc. of Dunedin, Fla.). A 1.2-mm fiber bundle was assembled to guide the light from the lasers to the test specimens and deliver the autofluorescence to the spectrometer. A universal serial bus (USB) connected the spectrometer to a computer for spectral recording. The extracted teeth were placed in a mounting fixture. A flexible fiber illuminated the teeth with either 405 nm or 532 nm laser. The collected fluorescence passed through an in-line filter to remove the excitation laser wavelengths before entering the spectrometer. The spectra were saved on a computer and analyzed offline.

Continuous wave output power was set to a constant at 1.34 mW for all lasers using an optical power meter (such as Model 1835-C developed by Newport Corporation of Irvine, Calif.). A 435 nm in-line longpass filter (such as GG 435 developed by Schott North America, Inc. of Elmsford, N.Y.), and a 532 nm in-line notch filter (such as NF01-532U-25-D developed by Semrock, Inc. of Rochester, N.Y.) were placed in series to attenuate both 405 nm and 532 nm excitation laser light at the spectrometer entrance aperture.

In the example, AF spectra excited by 405 nm and 532 nm lasers were obtained by manually alternating excitation of each individual laser on each specimen in the areas with signs of early stage caries. Additionally, AF from healthy enamel regions on each tooth was also recorded to obtain an intra-specimen standard. The spectrometer integration time was set to 100 ms to reduce system noise. Additional post filtering was then performed on the computer. For example, all emission spectra were filtered with a 13-point (corresponding to a spectral width of 4.94 nm) median filter to further remove electronic noise, followed by a 13-point Gaussian smoothing filter.

The emitted spectra from 405 nm and 532 nm excitation were obtained from different regions on the specimens that corresponded to different stages of enamel health. The spectrum curves were integrated to obtain the area-under-the-curve. The area of the 405 nm spectrum was then divided by the area of the 532 nm spectrum to obtain the dual laser fluorescence ratio metric.

All specimens examined in the example exhibited AF for 405 nm and 532 nm. A typical AF emission spectrum recorded from an early stage white spot lesion for both 405 nm excitation and 532 nm excitation is shown in FIG. 4. The spectrum from the 405 nm excitation shows broad emission centered around 480 nm and gradually tapers off toward the longer wavelengths. The spectrum from the 532 nm excitation is similar in shape but is shifted towards red with the peak fluorescence at around 580 nm. In this example, the dual laser ratio of area under the curve is 7.66.

The 405/532 nm AF ratio is obtained from the spectra by calculating the area of both curves and dividing the 405 nm area by the 532 nm area. FIG. 5 shows the mean 405/532 nm AF ratios for healthy, eroded, early stage white spot and brown spot enamel. Healthy enamel has the highest ratio, with a trend of decreasing ratio values as severity of lesion increased. Brown spot lesions had the lowest ratio among all enamel lesions.

There was statistical significance between healthy enamel and all other sample groups (4 hour erosion, 6 hour erosion, early white spot, and brown spot lesions) using two-tailed Student's T-tests for two samples with unequal size and variance at a 5% significance level. Table 3 shows Two-tailed Student's T-tests for two samples with unequal size and variance between the five groups (healthy, 4 hr erosion, 6 hr erosion, early white spot, and brown spot) at a 5% significance level. A 1 indicates significant statistical difference, while a 0 indicates no statistical difference.

TABLE 3

Results of statistical significance testing amongst all sample groups.

|  | Healthy | 4 Hr | 6 Hr | EWS | BS |
|---|---|---|---|---|---|
| Healthy | x | x | x | x | x |
| 4 Hr | 1 | x | x | x | x |
| 6 Hr | 1 | 0 | x | x | x |
| EWS | 1 | 0 | 0 | x | x |
| BS | 1 | 1 | 1 | 0 | x |

Table 4 shows the mean and standard error for 405/532 nm AF ratios. For each lesion classification, the ratio was computed for the lesion as well as for the healthy enamel surrounding the lesion. Percent change between the healthy and unhealthy enamel is also shown. The brown spot and early stage white spot lesions had the greatest percent change.

TABLE 4

Mean and standard error for 405/532 nm AF ratio of eroded and early stage caries lesions.

| Category | Mean Healthy Ratio | Mean Lesion Ratio | Percent Change |
|---|---|---|---|
| Artificial Erosion (4 hour) | 21.02 ± 7.36 | 12.58 ± 2.77 | 33.01 ± 27.68 |
| Artificial Erosion (6 hour) | 20.97 ± 8.13 | 11.37 ± 1.44 | 40.76 ± 17.69 |
| Early Stage White Spot | 24.22 ± 4.35 | 9.09 ± 3.92 | 62.27 ± 16.36 |
| Brown Spot | 26.44 ± 4.68 | 5.43 ± 1.3 | 79.63 ± 1.57 |

Figure 18A:
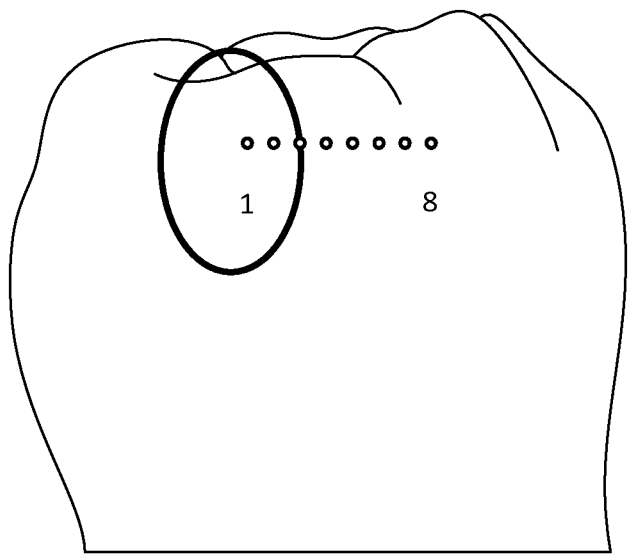
FIGS. 18a-b show a series of 405/532 nm AF ratio measurements progressively made from a natural white spot lesion to sound enamel, in accordance with an embodiment.
Figure 18B:
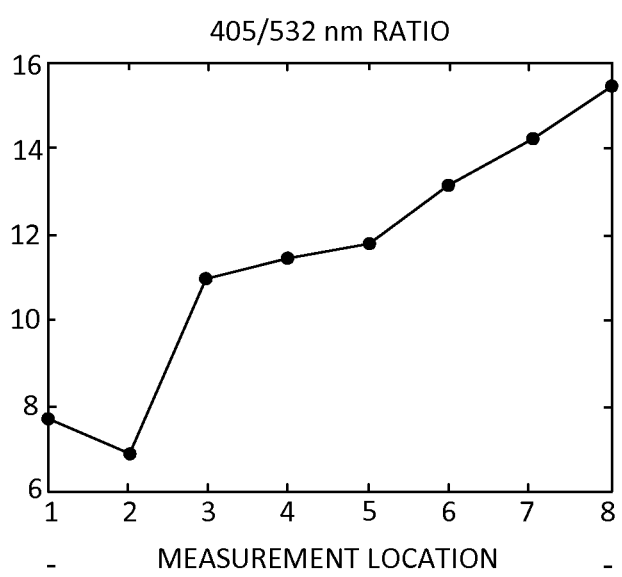

A series of 405/532 nm AF ratio measurements made from within a natural white spot lesion and progressing away from the lesion into the sound enamel is shown in FIG. 18. FIG. 18*a* shows an image taken of the tooth from the smooth surface. The locations of the spectral measurements are shown in dots. The visually difficult to perceive early stage white spot is highlighted by the circle. FIG. 18*b* shows AF ratios plotted against location on the tooth with measurement 1 inside the lesion and progressing away and into sound enamel (measurement 8). The AF ratio was low when within the white spot and progressively became larger as AF ratios were recorded from progressively healthier enamel. Almost 50 percentage change was found in this specimen between sound and caries enamel.

The 405/532 nm AF technique used in this example detects changes in the enamel micro-environment brought upon by demineralized enamel, which is the product of early stage caries. Also, using this dual laser method allows for an internal calibration since changes in topography, due to distance from the enamel surface to the fiber tip or angle of the enamel surface with respect to the fiber, will have an equal effect on both lasers. Thus, fluorescence intensity effects due to topography can be minimized when taking the ratio.

A low-cost benchtop or even handheld device to perform early carries detection in the developing world can be developed. Commercially available 405 nm and 532 nm lasers can now be purchased at low costs due to the commercial growth of Blu-Ray players, picoprojectors and green laser pointers. These lasers can be directly pulsed and interleaved by modulating the drive current and combined with disposable plastic transmit and return fibers to excite and collect the fluorescence emissions. Given the relatively broad emission spectra of the AF, much smaller and lower cost microspectrometers with high dynamic range CMOS detectors with 2-10+ nm resolution (such as STS-VIS developed by Ocean Optics, Inc. of Dunedin, Fla.) or even lower cost few wavelength spectral sensors can be used to obtain the relative intensities of the fluorescence. Laser timing and control, spectrometer I/O, radiometric calibration, and simple mathematical processes to obtain the AF ratio can all be done using simple microprocessors such as the Arduino (at www.arduino.cc). The obtained ratio can be then be classified as healthy or unhealthy and then the same microcontroller can be utilized to drive LED or LCD display functions.

To take a measure of early stage caries from a child, a wand can be developed that will be moved across a row of teeth, whereas an infant's few front teeth can be measured by developing a static lollipop device. In both cases, the device has cost and safety advantages compared to other means of assessing dental health, such as x-ray imaging and AF-reflectance imaging.

Preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for detecting dental demineralization, comprising:
    scanning a dental surface comprising directing excitation light at two or more excitation wavelengths to the dental surface, wherein the two or more excitation wavelengths include first light and second light from at least one laser, and wherein the second light has a longer wavelength than the first light;
    detecting light from the dental surface to obtain fluorescence emission spectral information respectively associated with the two or more excitation wavelengths for the dental surface, wherein the light from the dental surface includes a first emission spectrum corresponding to the first light and a second emission spectrum corresponding to the second light; and
    processing the fluorescence emission spectral information respectively associated with the two or more wavelengths so as to detect an area of demineralization near the dental surface, wherein the fluorescence emission spectral information includes a ratio of the first emission spectrum and the second emission spectrum.

2. The method of claim 1, wherein the fluorescence emission spectral information includes area-under-the-curve integrals each corresponding to the first emission spectrum and the second emission spectrum.

3. The method of claim 2, wherein each fluorescence emission spectrum comprises a range of wavelengths, each range of wavelengths substantially including at least a visible spectrum.

4. The method of claim 1, wherein the fluorescence emission spectral information includes peak intensities each corresponding to the first emission spectrum and the second emission spectrum.

5. The method of claim 1, wherein processing the fluorescence emission spectral information includes obtaining a ratio of area-under-the-curve integrals each corresponding to the first emission spectrum and the second emission spectrum.

6. The method of claim 4, wherein processing the fluorescence emission spectral information further includes comparing the ratio to a reference standard.

7. The method of claim 1, wherein the two or more excitation wavelengths include 405 nm and 532 nm.

8. The method of claim 1, further comprising:
    scanning a second dental surface comprising directing excitation light at the two or more excitation wavelengths to the second dental surface;
    detecting light from the second dental surface to obtain fluorescence emission spectral information respectively associated with the two or more excitation wavelengths for the second dental surface; and
    processing the fluorescence emission spectral information respectively associated with the two or more excitation wavelengths for the dental surface and the second dental surface so as to detect an area of dental demineralization near the second dental surface.

9. The method of claim 1, further comprising reducing specular reflection of emission fluorescence associated the two or more excitation wavelengths at least by:
    detecting the emission fluorescence with one or more sets of photo detectors; analyzing one or more sets of data respectively corresponding to the one or more photodetectors; and
    disregarding a subset of the one or more sets of data if the subset of data includes saturated data.

10. The method of claim 1, further comprising displaying an optical signal onto the dental surface, wherein the displayed optical signal is determined based on the processed fluorescence emission spectral information and indicates a dental condition associated with the dental surface.

11. A dental health screening system, comprising:
    an illumination source configured to provide light at two or more excitation wavelengths;
    a probe configured to illuminate a first dental area and a second dental area at the two or more excitation wavelengths, wherein the two or more excitation wavelengths include first light and second light from at least one laser, and wherein the second light has a longer wavelength than the first light;
    a spectrometer configured to provide fluorescence emission spectral information respectively associated with the two or more excitation wavelengths for the first dental area and for the second dental area, wherein the fluorescence emission spectral information is derived from a first emission spectrum corresponding to the first light and a second emission spectrum corresponding to the second light; and
    a computer system configured to:
        process the fluorescence emission spectral information respectively associated with the two or more excitation wavelengths for the first dental area and for the second dental area so as to detect an area of dental demineralization near the second dental area, wherein the fluorescence emission spectral information includes a ratio of the first emission spectrum and the second emission spectrum.

12. The system of claim 11, wherein the fluorescence emission spectral information includes area-under-the-curve integrals each corresponding to the first emission spectrum and the second emission spectrum.

13. The system of claim 11, wherein processing the fluorescence emission spectral information includes obtaining a ratio of area-under-the-curve integrals each corresponding to the first emission spectrum and the second emission spectrum.

14. The system of claim 11, wherein the probe is a scanning fiber endoscope (SFE).

15. The system of claim 11, further comprising one or more sets of photo detectors to detect reflectance or fluorescence and the system is configured to analyze one or more sets of data respectively corresponding to the one or more sets of photodetectors and disregard a subset of the one or more sets of data if the subset of data includes saturated data.

16. The system of claim 11, further comprising a disposable sleeve covering at least a portion of the probe to facilitate sterility.

17. The system of claim 16, wherein the probe is further configured to project a visual display onto the second dental area that indicates a result of the processing of the fluorescence emission spectral information by the computer system.

18. The system of claim 16, wherein the sleeve comprises one or more light collection channels.

19. The system of claim 16, wherein the sleeve comprises at least a fluid channel and a light collection channel.

20. The system of claim 11, wherein the probe is shaped like a lollipop to facilitate interrogation of the lingual side of one or more front teeth.

* * * * *